(12) United States Patent
Kovbasnjuk et al.

(10) Patent No.: US 7,875,586 B2
(45) Date of Patent: Jan. 25, 2011

(54) TREATMENT OF METASTATIC COLON CANCER WITH B-SUBUNIT OF SHIGA TOXIN

(75) Inventors: Olga N. Kovbasnjuk, Ellicott City, MD (US); Mark Donowitz, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 416 days.

(21) Appl. No.: 10/539,212

(22) PCT Filed: Dec. 20, 2003

(86) PCT No.: PCT/US03/40344
§ 371 (c)(1),
(2), (4) Date: Jun. 17, 2005

(87) PCT Pub. No.: WO2004/058158
PCT Pub. Date: Jul. 15, 2004

(65) Prior Publication Data
US 2007/0071772 A1 Mar. 29, 2007

Related U.S. Application Data

(60) Provisional application No. 60/435,139, filed on Dec. 20, 2002.

(51) Int. Cl.
*A61K 38/00* (2006.01)

(52) U.S. Cl. .......................................................... 514/12
(58) Field of Classification Search ...................... None
See application file for complete search history.

(56) References Cited

U.S. PATENT DOCUMENTS

2002/0081307 A1 * 6/2002 Green ..................... 424/184.1

OTHER PUBLICATIONS

Haicheur et al International Immunology vol. 15 p. 1161 (2003).*
Essell (J. NIH Res. 1995 7:46).*
Spitler (Cancer Biotherapy, 1995, 10:1-3).*
Boon (Adv. Can. Res. 1992 58:177-210).*
Webster'sII New Riverside University Dictionary (1984) p. 365.*
Strockbine et al J. Bacteriology vol. 170 p. 1116 (Mar. 1998).*
Accession No. 2002:397002 (Mar. 2002).*
Lacasse, E.C. et al., Shiga-Like Toxin purges Human Lymphoma From Bone Marrow of Severe Combined Immunodificient Mice. Blood. Sep. 1, 1996, vol. 88, No. 5, pp. 1561-1567.
Marcato, P. et al., Cloned Shiga Toxin B Sununit Induces Apoptosis in Ramos Burkitt's Lymphoma B cells. Infection and Immunity. Mar. 2002, vol. 70, No. 3, pp. 1279-1286.

* cited by examiner

*Primary Examiner*—Sheela J Huff
(74) *Attorney, Agent, or Firm*—Edwards Angell Palmer & Dodge LLP; Peter F. Corless

(57) ABSTRACT

The present invention relates to compositions and methods for treating invasive or metastatic cancer, particularly metastatic colon cancer using the B-submit of shiga toxin. The invention further provides methods of identifying compounds usefully for the treatment of invasive or metastatic cancer, particularly metastatic colon cancer.

10 Claims, 8 Drawing Sheets ive tumor cells. Accordingly, the present invention provides methods for the treatment of tumor metastasis, methods for determining whether tumor cells are capable of metastasizing, as well as methods for identifying compounds which can treat and/or prevent tumor invasion and metastasis.

TREATMENT OF METASTATIC COLON CANCER WITH B-SUBUNIT OF SHIGA TOXIN

CROSS-REFERENCES TO RELATED APPLICATIONS

The present application is the 35 U.S.C. §371 national stage of PCT application No. PCT/US03/40344, filed Dec. 20, 2003, and published in English, which claims benefit of U.S. Provisional Application Ser. No. 60/435,139, filed Dec. 20, 2002, the entire contents of which are hereby incorporated by reference.

BACKGROUND OF THE INVENTION

Colorectal cancer is the second leading cause of death from cancer in the USA (Yokota, *Carcinogenesis;* 121, 497-503; 2000). The high mortality associated with colorectal cancer is related to its ability to spread beyond the large intestine and invade distant organs. Therefore, increasing efforts are being focused on developing more effective screening for colon cancer invasion and metastatic markers (Saha et al, *Science,* 294, 1343-1346; 2001; Buckhaults et al., *Cancer Res.,* 61, 6996-7001; 2001), based on differences in protein expression between normal colonic and cancer tissue. Several proteins which are upregulated in colon cancer have been shown to increase the metastatic potential. However, an understudied area is changes in cellular glycosphingolipid (GSL) production, which are known to accompany the transformation of colon cancer cells into metastatic cells. GSL are the major structural components of the cell membrane. They are also important functional components of lipid rafts (LR) and are involved in many cell signaling pathways (Anderson and Jacobson, *Science,* 296, 1821-1825; 2002). GSL change dramatically in quantity and quality during cell differentiation or malignant transformation (Hakomori and Kannagi, *J. Natl. Cancer Inst.,* 71, 21-34; 1983: Hakomori, *Cancer Res.,* 56, 5309-5318; 1996). Abberant glycosylation occurs essentially in all types of cancers and some aberrant glycosylation is a result of initial oncogenic transformation, as well as a key event in induction of invasion and metastasis (Hakomori, *Adv Cancer Res.,* 52, 257-331; 1989, *Proc Natl Acad Sci USA,* 99, 10231-10233; 2002). For example, it is well established that $G_{M3}$ inhibits cell motility and invasiveness in bladder tumor (awamura et al., *Proc Natl Acad Sci USA,* 99, 10718-23; 2001). Ganglioside $Gt_{1b}$, $GD_{1A}$ and $G_{M1}$ inhibit cell proliferation and epidermal growth factor receptor tyrosine phosphorylation (Mirkin et al, *Cell Prolif.,* 35, 105-115; 2002). However, a different GSL $G_{b5}$ strongly enhances motility in experiments with breast cancer cells (Hakomori, *Proc Natl Acad Sci USA,* 99, 10231-10233; 2002). Recently enhanced expression of the ganglioside-specific sialidase "Neu3" was reported in colorectal cancer (Kakugawa et al., *Proc Natl Acad Sci USA,* 99, 10718-23; 2002), indicating that GSL function in tumor progression may have been underestimated.

SUMMARY OF THE INVENTION

The present invention is based on the discovery that glycosphingolipid (GSL) globotriaosylceramide ($Gb_3$) is a marker for potentially invasive human colon cancer cells. Specifically, the present invention is based on the discovery that $Gb_3$ production or content is significantly elevated in metastatic human colon cancer compared to non-metastatic colon cancer and non-cancerous tubular colon adenomas. The present invention is further based on the discovery that $Gb_3$ production turns non-invasive epithelial cells into invasive ones. Furthermore, the present invention relates to the Shiga toxin 1 B-subunit (hereafter referred to as "Stx1B") and the Shiga toxin 2 B-subunit (hereafter referred to as "Stx2B"), both of which bind $Gb_3$ on the surface of cells and selectively kill invasive colon tumor cells. Accordingly, the present invention provides methods for the treatment of tumor metastasis, methods for determining whether tumor cells are capable of metastasizing, as well as methods for identifying compounds which can treat and/or prevent tumor invasion and metastasis.

Accordingly, in one embodiment, the present invention provides methods of preventing, reducing, or inhibiting invasion and metastasis of tumor cells in a subject (e.g., a human subject) comprising administering to the subject a therapeutically effective amount of Stx1B and/or Stx2B. The tumor cells may be derived from any tissue, including, but not limited to colon, lung, brain, skin, ovary, pancreas, liver, stomach, bladder, bone, testicle, uterus, adipose tissue, throat, kidney, tongue, pituitary gland, thyroid, lymphoid tissue, eye, and cervix. Preferably, the tumor cells are colon tumor cells.

In one embodiment, the B-subunit of Shiga toxin of administered prior to the onset of metastasis by the tumor cells. In another embodiment, it is administered subsequent to the onset of metastasis by the tumor cells.

In further embodiments, the methods comprise administering the B-subunit of Shiga toxin in conjunction with other cancer therapies, including radiation and chemotherapy.

In another embodiment, the invention provides methods of identifying compounds capable of preventing, reducing, or inhibiting tumor cell metastasis comprising contacting a cell that produces $Gb_3$ with a test compound, and measuring $Gb_3$ production or activity by the cell, wherein a compound which reduces or inhibits $Gb_3$ production by the tumor cells is identified as a compound capable of preventing, reducing, or inhibiting tumor cell invasion and metastasis. $Gb_3$ production may be measured, for example, by measuring the level of $Gb_3$ Synthetase mRNA (e.g., using Northern blotting, RNAse protection, primer extension, and/or RT-PCR) or $Gb_3$ lipid (e.g., using chromatography, ELISA, RIA, FACS, and immunocytochemistry). This invention also can be used to diagnose the location of invasive or metastatic colon cancer cells.

Other features and advantages of the invention will be apparent to those skilled in the art from the following detailed description and claims.

BRIEF DESCRIPTION OF THE DRAWINGS

FIG. 1A: Human colon cancer tissue (n=29 samples from 5 subjects). FIG. 1B: Human non-malignant tubular adenomas (n=20 samples from 5 subjects). FIG. 1C: Colon cancer metastases into the liver (n=17 samples from 2 of the subjects used in FIG. 1A). FIG. 1D: Normal liver tissue (n=10 samples from 2 subjects).

FIG. 2A: XY-plane from a 3-dimentional reconstruction of fluorescent confocal optical sections of representative Caco-2 cells with $Gb_3$-containing filopodia marked by Stx1B-OrG. Filopodia and filopodia-containing cells are significantly enriched in $Gb_3$ positive cells compared to the rest of the cells from leading edge, bar—10 μm. FIG. 2B: XZ-projection from a 3-dimentional reconstruction of fluorescent confocal optical sections of representative Caco-2 cell with $Gb_3$-containing filopodia, which is significantly taller than adjacent cells in the monolayer. Vertical bar—25 μm. FIGS. 2C and 2D: Appearance of $Gb_3$-enriched filopodia-containing cells in (FIG. 2C) the HT-29 monolayers and (FIG. 2D) on the leading edge of T84 monolayer.

FIGS. 3A-3D, 3I (left panel), and 3II (left panel) show detection of Stx1B-OrG fluorescence. FIGS. 3E, 3F, 3I (middle panel), and 3II (middle panel) show detection of CTB-TRITC fluorescence. FIGS. 3G, 3H, 3I (right panel), and 3II (right panel) show merged detection of both Stx1B-OrG and CTB-TRITC fluorescence. FIG. 3A: Confluent monolayer on the top of the filter. FIG. 3B: Section through the filter. FIGS. 3C and 3D: $Gb_3$-enriched, filopodia-containing cells invading the bottom surface of filter. FIG. 3E: Subconfluent OK cells labeled by Cyto7 dye do not express $Gb_3$ and do not form a filopodia on the leading edge. FIG. 3F: OK cells do not invade the bottom surface of the membrane, but form a monolayer on the top surface of the filter only. FIG. 3G: OK cells transfected with Gb3-synthase are able to form $Gb_3$-enriched filopodia. FIG. 3H: Only $Gb_3$-expressing OK cells invaded bottom surface of membrane. FIGS. 3I and 3II: $Gb_3$ appears before $G_{M1}$ in newly formed filopodia in Caco-2 cells. FIG. 3I: Time 0. FIG. 3II: The same cells 75 mnin later.

FIG. 4A: $Gb_3$ staining by Stx1B-OrG. FIG. 4B: F-actin staining with TRITC-phalloidin of the same cell as in FIG. 4A. FIG. 4B: α-Tubulin. FIG. 4D-F: The effect of Rho kinase inhibitor Y-27632 (2 μg/ml) on filopodia and filopodia-containing cells. FIG. 4D: Filopodia-containing cells before treatment with Y-27632. FIG. 4E: After 30 min incubation with Y-27632. FIG. 4F: After 60 min incubation with Y-27632. Bar—10 μm. FIG. 4G: Protein contents and distribution between DS and DIM fractions from filopodia and cell bodies. FIG. 4H: An example of Western blot analysis using monoclonal anti-$Gb_3$ CD77 antibody, which allows detection of proteins complexed with $Gb_3$. The protein in this figure was identified by mass spectroscopy as human β-tubulin.

FIG. 6A: Intact mitochondria in control Caco-2 cells 24 hours after toxin exposure. FIG. 6B: Depolarized mitochondria in Caco-2 cells exposed to recombinant Stx1B for 12 hours. Only cells which accumulated Stx1B in Caco-2 monolayers have depolarized mitochondria and do not accumulate TMRE dye, while neighboring cells with no or less Stx1B inside have functional mitochondria labeled byTME. FIGS. 6C and 6D: Intact mitochondria in control OK (FIG. 6C) and intact mitochondria in OK cells exposed to Stx1B (FIG. 6D) for 12 hours.

DETAILED DESCRIPTION OF THE INVENTION

Figure 1:
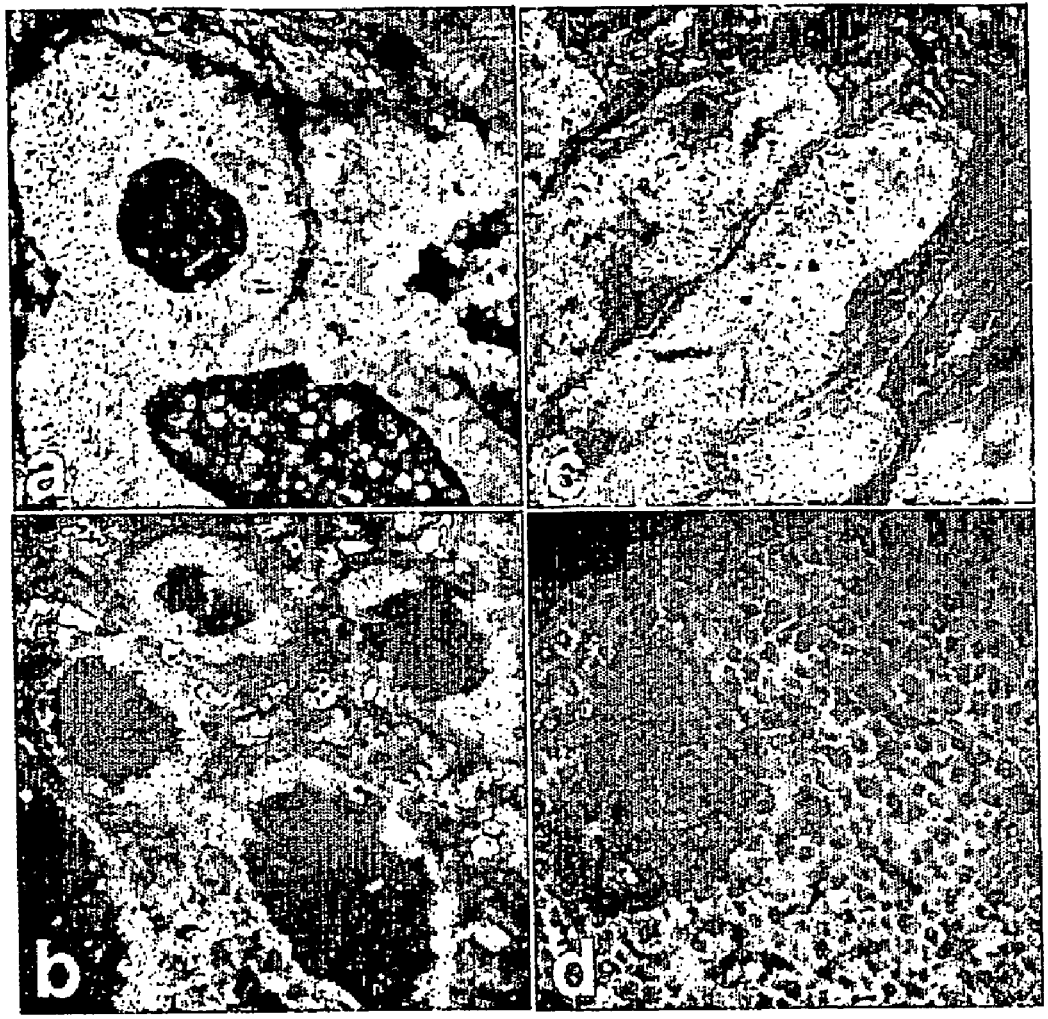
FIGS. 1A-1D depict the increase in $Gb_3$ production in primary human metastatic colon cancer with liver metastases. Representative confocal optical sections of human tissue immunostained with antibodies against β-catenin, $Gb_3$ marked by OrG-Stx1B, and nuclear staining by Hoest.

The present invention is based on the discovery that glycosphingolipid (GSL) globotriaosylceramide ($Gb_3$) is a marker for potentially invasive and metastatic human colon cancer cells. Specifically, the present invention is based on the discovery that $Gb_3$ is significantly elevated in metastatic human colon cancer compared to non-metastatic colon cancer and non-cancerous tubular colon adenomas. The present invention is further based on the discover that $Gb_3$ expression turns non-invasive epithelial cells into invasive ones, and that Shiga toxin 1 B-subunit can selectively kill invasive colon tumor cells. Accordingly, the present invention provides methods for the treatment of tumor metastasis, methods for determining whether tumor cells are capable of metastasizing, methods for identifying compounds which can treat tumor invasion and metastasis, as well as diagnostic methods to identify where tumor has invaded or metastasized.

The greatest threat from tumors comes from metastasis—the spread of cancer cells from the primary tumors into different organs. The steps involved are local invasion allowing cells to escape their initial tissue and then metastasize or establishing tumors on sites different from the original tissue.

Shiga toxin 1 (Stx1), which is expressed by enterohemorrhagic *E. coli* or *Shigella dysenteriae*, specifically binds to $Gb_3$. Stx1 contributes to the spectrum of disease including watery and bloody diarrheas, hemolytic uremic syndrome, and in some cases, encephalopathy. Pathophysiological effects of Stx1 on intestinal epithelium include mucosal damage with villus shortening, extensive inflammation, and fluid accumulation (Acheson, D. W. K., Donohue-Rolfe, A., Keusch G. T. 1991. The family of Shiga and Shiga-like toxins. P. 415-433. In J. E. Aloufand and J. H. Freer (ed.), Sourcebook of bacterial protein toxin. Academic Press Ltd., London, UK).

Stx1 represents a broad class of so-called $AB_5$ bacterial toxins. It consists of a single A-subumt, which possesses a toxic N-glycosidase activity that inhibits protein synthesis through specific removal of the adenine base at position 4324 of the 28S ribosomal RNA of the 60S subunit of eucaryotic ribosomes (Sjogren R, Neill R, Rachmilewitz D, Fritz D, Newland J, Sharpnack D, Colleton C, Fondacaro J, Gemski P, Boedeker E. 1994. Role of Shiga-like toxin I in bacterial enteritis: comparison between isogenic *Escherichia coli* strains induced in rabbits. *Gastroenterology*. 106:306-317.). A pentamer of identical B-subunits is responsible for the receptor binding function and intracellular trafficking (Donohue-Rolfe A, Keusch G T, Edson C, Thorley-Lawson D, Jacewicz M. 1984. Pathogenesis of *Shigella diarrhea*. 9. Simplified high-yield purification of shigella toxin and characterization of subunit composition and function by the use of subunit-specific monoclonal and polyclonal antibodies. *J. Exp. Med.* 160: 1767-1781.; Lacy, D. B., Stevens R. C. 1998. Unraveling the structures and modes of action of bacterial toxins. *Cur. Opin. Struct. Biol* 8: 778-784.). The functional receptor of Stx1 is the neutral glycolipid $Gb_3$ which has terminal sugar residues αGal(1-4)βGalβGlc-ceramide (Acheson D W K, Moore R, DeBreucker S, Lincicome L, Jacewicz M, Skutelsky E, Keusch GT. 1996. Translocation of Shiga toxin across polarized Intestinal cells in tissue culture *Infect. Immun.* 64: (8) 3294-3300; Donohue-Rolfe A, Jacewicz M., Keusch G T. 1989. Isolation and characterization of functional Shiga toxin subunits and renatured holotoxin. *Mol. Microbiol.* 3: 1231-1236; Waddell T, Head S, Petric M, Cohen A, Lingwood C. 1988. Globotriosyl ceramide is specifically recognized by the *Escherichia coli* verocytotoxin-2. *Biochem. Bioph. Res. Com.* 152: 674-679).

The sequences of numerous Shiga toxin variants and subunits are known in the art. For example, the Shiga toxin 1 B-subunit from the *E. coli* O157:H7 strain is set forth in GenBank Accession Nos. 32400300 and 32400303, the Shiga toxin 2 B-subunit from the *E. coli* O157:H7 strain is set forth in GenBank Accession No. 13359150, the Shiga toxin 1 A-subunit is set from the *E. coli* O157:H7 strain is set forth in GenBank Accession Nos. 32400299 and 32400302, and the Shiga toxin 2 A-subunit from the *E. coli* O157:H7 strain is set forth in GenBank Accession No. 15718405.

The cytotoxic effects of Stx1 were originally thought to be due only to the inhibition of protein synthesis mediated by the A-subunit of the toxin (Obrig T G, Moran T P, Brown J E. 1987. The mode of action of shiga toxin on peptide elongation of eukaryotic protein-synthesis. *Biochem. J.* 244: 287-294; Endo Y, Tsurugi K, Yutsudo T, Takeda Y, Ogasawara T, Igarashi K. 1988. Site of action of a Vero toxin (VT2) from *Escherichia-Coli* and of Shiga toxin on eukaryotic ribosomes RNA N-glycosidase activity of the toxins. *Europ. J Biochem.* 171: 45-50; Saxena S K, Obrien A D, Ackerman E J. 1989. Shiga toxin, Shiga-like toxin-ii variant, and ricin are all single-site RNA N-glycosidases of 28-S RNA when microinjected into Xenopus oocytes. *J. Biol. Chem.* 264: 596-601). Recently, however, several reports have claimed that Stx1 mediates apoptotic cell death, including in renal tubular and pulmonary epithelial cells (Iaward C D, Williams J, Chant I, Crocker J, Milford D V, Rose P E, Taylor CM. 1995. Verocytotoxin-1 induces apoptosis in Vero cells. *J. Infec.* 30: 213-218; Kiyokawa N, Mori T, Taguchi T, Saito M, Mimori K, Suzuki T, Sekino T, Sato N, Nakajima H, Katagiri Y U, Takeda T, Fujimoto J. 2001. Activation of the caspase cascade during Stx1-induced apoptosis in Burkitt's lymphoma cells. *J. Cell. Biochein.* 81: 128-142; Kaneko K, Kiyokawa N, Ohtomo Y, Nagaoka R, Yamashiro Y, Taguchi T, Mori T, Fujimoto J, Takeda T. 2001. Apoptosis of renal tubular cells in shiga-toxin-mediated hemolytic uremic syndrome. *Nephron* 87: 182-185; Jones N L, Islur A, Haq R, Mascarenhas M, Karmali M A, Perdue M H, Zanke B W, Sherman P M. 2001. *Escherichia coli* Shiga toxins induce apoptosis in epithelial cells that is regulated by the Bc1-2 family. *Am. J. Physiol.* 278: G811-G819.). Also, B-subunit alone in much higher concentrations than holotoxin triggers apoptosis in BL and HEp-2 cells (Jones N L, Islur A, Haq R, Mascarenhas M, Karmali M A, Perdue M H, Zanke B W, Sherman P M. 2001. *Escherichia coli* Shiga toxins induce apoptosis in epithelial cells that is regulated by the Bc1-2 family. *Am. J. Physiol.* 278: G811-G819.; Gordon J, Challa A, Levens J M, Gregory C D, Williams J M, Armitage R J, Cook J P, Roberts L M, Lord J M. 2000. CD40 ligand, Bc1-2, and Bc1-x(L) spare group I Burkitt lymphoma cells from CD77-directed killing via Verotoxin-1 B chain but fail to protect against the holotoxin. *Cell Death Differ.* 7: 785-794), while TBP-1 cells, which bind Stx1, are insensitive to B-subunit treatment (Mangeney M, Lingwood C A, Taga S, Caillou B, Tursz T, Wiels J. 1993. Apoptosis induced in Burkitts lymphoma cells via GB3/CD77, a glycolipid antigen. *Cancer Res.* 53: 5314-5319).

Apoptosis has been recognized as a physiologically normal form of cell death and plays a crucial role in the development and maintenance of homeostasis of tissues (Li H, Yuan J. 1999. Deciphering the pathways of life and death. *Curr Opin Cell BioL* 11:261-266.). Apoptosis is characterized by specific morphological changes such as cell shrinkage, condensation of nuclei and loss of microvilli as well as chromosomal DNA cleavage (Li H, Yuan J. 1999. Deciphering the pathways of life and death. *Curr Opin Cell BioL* 11:261-266.; Thomberry N A, Lazebnik Y. 1998. Caspases: Enemies within. *Science* 281: 1312-1316). Although a number of distinct pathways that mediate apoptosis have been identified, a major molecular modulator of apoptosis is the Bc1-2 family of proteins, which contains both proapoptotic proteins such as Bax and antiapoptotic members such as Bc1-2 (Adams J M, Cory S. 1998. The Bc1-2 protein family: Arbiters of cell survival. *Science* 281: 1322-1326). Bax induces the release of mitochondrial cytochrome c and triggers caspase activation, while Bc1-2 is capable of preventing Bax-mediated cell death (Krebs J F, Armstrong R C, Srinivasan A, Aja T, Wong A M, Aboy A, Sayers R, Pham B, Vu T, Hoang K, Karanewsky D S, Leist C, Schmitz A, Wu J C, Tomaselli K J, Fritz L C. 1999. Activation of membrane-associated procaspase-3 is regulated by Bc1-2. *J. Cell Biol.* 144:915-26.). Caspases (cysteine proteases) are thought to be essential as effector molecules in the apoptotic process in most cases (Los M, Wesselborg S, Schulze-Osthoff K. 1999. The role of caspases in development, immunity, and apoptotic signal transduction: lessons from knockout mice. *Immunity* 10:629-639.; Nicholson D W, Ali A, Thomberry N A, Vaillancourt J P, Ding C K, Gallant M, Gareau Y, Griffin P R, Labelle M, Lazebnik Y A. 1995. Identification and inhibition of the ICE/CED-3 protease necessary for mammalian apoptosis. *Nature* 376:37-43.). Cancers generally have decreased apoptosis and increasing apoptosis is an accepted strategy for killing cancer cells.

One of the major problems in cancer treatment is the non-specificity of drugs, which kill not only potentially invasive cancer cells, but also adjacent non-cancer cells. Because $Gb_3$ is expressed selectively in potentially metastatic colon tumor cells, but not in normal colonic epithelia or non-cancerous adenomas and non-metastatic colon cancer cells, Stx1B and Stx2B can be used to selectively target and kill metastatic and/or potentially metastatic cancer cells. Additionally, there is evidence that GSL-enriched cells in tumors represent the potentially metastatic pool of cells which is highly resistant to chemotherapeutic agents, and which causes the major threat to survival in colon cancer. The use of Stx1B and Stx2B, both, alone and/or respectively conjugated to additional therapeutic agents, represents a method for eliminating this invasive and potentially metastatic cell population.

I. Definitions

As used herein, the terms "neoplastic cells", "neoplasia", "tumor", "tumor cells", "cancer" and "cancer cells" (used interchangeably) refer to cells which exhibit relatively autonomous growth, so that they exhibit an aberrant growth phenotype characterized by a significant loss of control of cell proliferation. Neoplastic cells can be malignant or benign.

As used herein, "suppressing tumor growth" refers to reducing the rate of growth of a tumor, halting tumor growth completely, causing a regression in the size of an existing tumor, eradicating an existing tumor and/or preventing the occurrence of additional tumors upon treatment with the compositions, kits, and/or methods of the present invention. "Suppressing" tumor growth indicates a growth state that is curtailed when compared to growth by cells treated not treated using the compositions, kits, and/or methods of the present invention. Tumor cell growth can be assessed by any means known in the art, including, but not limited to, directly measuring tumor size, radiographic imaging, utilizing serum biomarkers of disease burden, determining whether tumor cells are proliferating using a $^3$H-thymidine incorporation assay or clonogenic assay, or counting tumor cells.

"Suppressing" tumor cell growth means any or all of the following states: slowing, delaying, preventing and stopping tumor growth, as well as tumor shrinkage.

"Invasion and Metastasis" of tumor cells refers to two mechanisms by which cancer cells spread through the body. Invasion is the direct migration and penetration by cancer cells into neighboring tissues. Metastasis is the ability of cancer cells to penetrate into lymphatic and blood vessels, circulate through the bloodstream, and then grow in a new focus (metastasize) in normal tissues elsewhere in the body. During metastasis, tumor cells penetrate the fibrous boundaries that normally separate one tissue from another. The tumor can also infiltrate the walls of blood or lymph vessels and shed cancer cells into the circulation. In the blood, these tumor cells are carried downstream to become lodged in the next capillary bed. Tumor cells shed from colon cancer, for example, are carried by the circulation to the liver, where secondary tumors then arise. Tumor cells from other areas of the body can be carried by the blood through the heart and on to the lungs, where they start metastatic lung tumors. Tumor cells shed into the lymph system often establish themselves in the nearest cluster of lymph nodes, where they grow before spreading to more distant parts of the body. Fewer than 1 in 10,000 cells shed from the primary tumor are thought to survive, but these are enough to spawn secondary tumors elsewhere in the body.

"Delaying development" of a tumor means to defer, hinder, slow, retard, stabilize, and/or postpone development of the disease. This delay can be of varying lengths of time, depending on the history of the disease and/or individual being treated. The present invention provides for both prophylactic and therapeutic methods of treating a subject at risk of (or susceptible to) developing cancer, e.g., a disorder associated with aberrant or unwanted Gb$_3$ expression or activity.

As used herein, "treatment" of a subject includes the application or administration of a therapeutic agent to a subject, or application or administration of a therapeutic agent to a cell or tissue from a subject, who has a diseases or disorder, has a symptom of a disease or disorder, or is at risk of (or susceptible to) a disease or disorder, with the purpose of curing, healing, alleviating, relieving, altering, remedying, ameliorating, improving, or affecting the disease or disorder, the symptom of the disease or disorder, or the risk of (or susceptibility to) the disease or disorder. As used herein, a "therapeutic agent" includes, but is not limited to, small molecules, peptides, polypeptides, antibodies, ribozymes, and antisense oligonucleotides.

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector.

The terms "polynucleotide" and "nucleic acid", used interchangeably herein, refer to a polymeric form of nucleotides of any length, either ribonucleotides and/or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH$_2$) or a mixed phosphoramidate-phosphodiester oligomer. Peyrottes et al. (1996) Nucleic Acids Res. 24: 1841-8; Chaturvedi et al. (1996) Nucleic Acids Res. 24: 2318-23; Schultz et al. (1996) Nucleic Acids Res. 24: 2966-73. A phosphorothioate linkage can be used in place of a phosphodiester linkage. Braun et al. (1988) J. Immunol. 141: 2084-9; Latimer et al. (1995) Molec. Immunol. 32: 1057-1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. Reference to a polynucleotide sequence (such as referring to a SEQ ID NO) also includes the complement sequence.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example those described in Current Protocols in Molecular Biology (F. M. Ausubel et al., eds., 1987) Supplement 30, section 7.7.18. A preferred alignment program is ALIGN Plus (Scientific and Educational Software, Pennsylvania), preferably using default parameters, which are as follows: mismatch=2; open gap=0; extend gap=2.

"Under transcriptional control" is a term well understood in the art and indicates that transcription of a polynucleotide sequence, usually a DNA sequence, depends on its being operably (operatively) linked to an element which contributes to the initiation of, or promotes, transcription. "Operably linked" refers to a juxtaposition wherein the elements are in an arrangement allowing them to function.

The term "heterologous" means a DNA sequence not found in the native vector genome. With respect to a "heterologous transcriptional regulatory sequence", "heterologous" indicates that the transcriptional regulatory sequence is not naturally ligated to the DNA sequence for the gene essential for replication of the vector.

The term "promoters" is used according to its art-recognized meaning. It is intended to mean the DNA region, usually upstream to the coding sequence of a gene or operon, which binds RNA polymerase and directs the enzyme to the correct transcriptional start site.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, farm animals, sport animals, rodents, primates, and pets An "therapeutically effective amount" is an amount sufficient to effect beneficial or desired results, including clinical results. An effective amount can be administered in one or more administrations. For purposes of this invention, an effective amount of Stx1B protein is an amount that is sufficient to palliate, ameliorate, stabilize, reverse, prevent, slow or delay the progression of the disease state.

"Expression" includes transcription of nucleotides and/or translation of nucleotide codons into amino acids of proteins, peptides and/or polypeptides.

"Production" (including producing and produces) refers to the intracellular generation of a cellular component, most particularly in the case of the present invention, the glycosphingolipid, globotriaosylceramide ($Gb_3$). The generation of $Gb_3$ can be the result of increased cellular synthesis and/or decreased degradation of $Gb_3$. Cancer cells are found to produce and contain higher levels of $Gb_3$ than normal cells. Furthermore, the production of $Gb_3$ in cancer cells confers the ability of cells to invade neighboring tissues, as well as infiltrate blood and lymphatic vessels leading to cancer cell metastasis.

II. Methods of Treatment

In one embodiment, the present invention provides methods of preventing, reducing, or inhibiting invasion and metastasis of tumor cells in a subject (e.g., a human subject) comprising administering to the subject a therapeutically effective amount of the B-subunit of Shiga toxin, (Stx1B and/or Stx2B) or either a Stx1B conjugate or a Stx2B conjugate. The tumor cells may be derived from any tissue, including, but not limited to colon, lung, brain, skin, ovary, pancreas, liver, stomach, bladder, bone, testicle, uterus, adipose tissue, throat, kidney, tongue, pituitary gland, thyroid, nerve, lymphoid tissue, eye, and cervix. Preferably, the tumor cells are colon tumor cells.

In one embodiment, the Stx1B and/or Stx2B and/or their respective conjugates is/are administered prior to the onset of metastasis by the tumor cells. In another embodiment, the agent(s) is administered subsequent to the onset of metastasis by the tumor cells.

In further embodiments, the methods comprise administering Stx1B and/or Stx2B and/or their respective conjugates in conjunction with other cancer therapies, including radiation and chemotherapy.

In still further embodiments, the methods of the invention comprise administering to the subject an inhibitor of $Gb_3$ production and/or activity. Inhibitors of $Gb_3$ production and/or activity include, but are not limited to, Stx1B, Stx2B and their respective conjugates, as well as any other compound which can inhibit $Gb_3$ production and/or activity, for example, an inhibitor of the $Gb_3$ synthesis pathway (e.g., an inhibitor of $\alpha$1,4-galacosyltransferase, also known as $Gb_3$ synthase). Such compounds may be identified, for example, using the screening assays described herein.

As used herein, "treatment" of a subject includes the application or administration of a therapeutic agent (e.g., B-subunit of shiga toxin) to a subject, or application or administration of a therapeutic agent to a cell or tissue from a subject, who has a diseases or disorder (e.g., cancer), has a symptom of a disease or disorder, or is at risk of (or susceptible to) a disease or disorder, with the purpose of curing, healing, alleviating, relieving, altering, remedying, ameliorating, improving, preventing, diagnosing or affecting the disease or disorder, the symptom of the disease or disorder, or the risk of (or susceptibility to) the disease or disorder.

In some embodiments, the methods of the present invention provide for suppressing tumor growth (e.g., suppressing growth of metastases). In other embodiments, the methods are for reducing size and/or extent of a tumor (e.g., a metastatic tumor). In other embodiments, the methods are for delaying development of a metastatic tumor. In other embodiments, the methods are for treating a neoplasia. In still other embodiments, the methods are for killing tumor cells.

Individuals suitable for treatment by these methods include individuals who have or are suspected of having cancer, including individuals in the early or late stages of the disease, as well as individuals who have previously been treated or are about to undergo treatment (e.g., are in the adjuvant or neoadjuvant setting). Other individuals suitable for the methods described herein are those who are considered high risk for developing a tumor, such as those who have a genetic predisposition to development of a neoplasia and/or who have been exposed to an agent(s) which is correlated with development of a neoplasia. Preferably, the methods of the invention are used to treat individuals having metastatic tumors (e.g., metastatic colon cancer). The B subunit also can be used to check if an individual has invasive or metastatic disease at any time in the course of the disease. By placing a clinically detectable tag on the Shiga toxin B subunit, tumor cells that have $Gb_3$ content and are potentially invasive or metastatic, or have invaded or metastasized can be detected. Thus, the invention includes diagnostic tests for cancer invasion and metastasis.

The presence of cancer and the suitability of the individual for receiving the methods described herein may be determined by any of the techniques known in the art, including diagnostic methods such as imaging techniques, analysis of serum tumor markers, and biopsy.

In another embodiment, the methods of the invention can be administered in conjunction with other known treatments for cancer, including, but not limited to, mechanical removal of cancerous cells (e.g., surgical removal of a tumor), radiation treatment, and administration of chemotherapeutic agents. In addition to DNA-damaging agents, there are many other chemotherapeutic agents used to treat cancer which act to kill cancer cells and/or slow their growth through other mechanisms. The administration of such additional treatments and/or agents are intended to be included in the methods of the present invention.

As used herein, a "DNA-damaging agent" is any agent or treatment that, when administered to a cell or a subject, e.g., a human subject, cause damage to the cell or subject's DNA (e.g., genomic DNA). In one embodiment, the DNA-damaging agent is radiation. In another embodiment, the DNA-damaging agent is a chemotherapeutic agent. Preferred chemotherapeutic DNA-damaging agents include, but are not limited to, alkylating agents such as nitrogen mustards (e.g., chlorambucil, cyclophosphamide, estramustine, ifosfamide, mechlorethamine, and melphalan), aziridines (e.g., thiotepa), alkyl sulfonates (e.g., busulfan and methyl methanesulfonate (MMS)), nitrosureas (e.g., carmustine, lomustine, and streptozocin), platinum complexes (e.g., carboplatin and cisplatin), and nonclassic alkylators (e.g., altretaniine, dacarbazine, procarbazine, and temozolamide). In some embodiments, the methods of the present invention comprise the use of one or more DNA-damaging agents.

Other chemotherapeutic agents that may be used in conjunction with the methods of the invention include, but are not limited to, antimetabolites such as folate analogs (e.g., methotrexate), purine analogs (e.g., fludarabine, mercaptopurine, and thioguanine (e.g., 6-TG)), adenosine analogs (e.g., cladribine, and pentostatin), pyrimidine analogs (e.g., capecitabine, cytarabine, depocyt, floxuridine, fluorouracil (e.g., 5-FU), and gemcitabine), and substituted ureas (e.g., hydroxyurea); natural products such as antitumor antibiotics (e.g., bleomycin, dactinomycin, actinomycin D, daunorubicin, daunomycin, DaunoXome (liposomal daunorubicin), doxorubicin, Doxil (liposomal doxorubicin), epirubicin, idarubicin, mitoxantrone, and mitomycin C), epipodophyllotoxins (e.g., etoposide and teniposide), microtuble agents (e.g., docetaxel, paclitaxel, vinblastine, vincristine, and vinorelbine), camptothecin analogs (e.g., irinotecan and topotecan), enzymes (e.g., asparaginase), and monoclonal antibodies (e.g., alemtuzamab, gemtuzumab ozogamicin, ibritumomab tiuxetan, nofetumomab, rituximab, tositumomab, and trastuzumab). Any of these agents which have DNA-damaging activity may also be used directly in the methods of the invention.

Still further chemotherapeutic agents that may be used in conjunction with the methods of the invention include, but are not limited to, aldesleukin, alitretinoin, allopurinol, altretamine, amifostine, anastrozole, arsenic trioxide, bexarotene, calusterone, capecitabine, celecoxib, cimetidine, darbepoetin alfa, denileukin diftitox, dexamethazone, dexrazoxane, diphenhydramine, dromostanolone propionate, epoetin alfa, estramustine, exemestane, filgrastim, floxuridine, fludarabine, flutamide, fulvestrant, goserelin, imatinib mesylate, interferon alfa-2a, interferon alfa-2b, letrozole, leucovorin, leuprolide, levamisole, megestrol acetate, mercaptopurine (e.g., 6-MP), mesna, methoxsalen, mitotane, nandrolone phenpropionate, oprelvekin, oxaliplatin, pamidronate, pegademase, pegaspargase, pegfilgrastim, pentostatin, pipobroman, plicamycin, mithramycin, porfimer sodium, prednisone, quinacrine, ranitidine, rasburicase, sargramostim, talc, tamoxifen, testolactone, toremifene, tretinoin, uracil mustard, valrubicin, and zoledronate. Those of skill in the art will recognize that any of these chemotherapeutic agents may fit into one or more particular classes of chemotherapeutic agents described above, including DNA-damaging agents.

Stx1B and Stx2B, through a protein ligation technique (Z. Zhang, et al; JBC 278:4668-4671; 2002) can be conjugated to any conventional chemotherapeutic drug and be used as a drug delivery system, specifically directed to potentially invasive and/or metastatic cancer cells and selectively kill the cells.

Those of skill in the art will appreciate that preferred dosage levels and schedules are well-known in the field of cancer treatment. Accordingly, in one embodiment, the methods of the invention will be used in accordance with standard dosage levels and schedules for the DNA-damaging agents. A useful general resource for methods of treating and managing cancer is Pazdur, R. et al., eds., *Cancer Management: A Multidiscliplinary Approach,* 7$^{th}$ *edition.* The Oncology Group, a division of SCP Communications, Inc., New York: 2003. Non-limiting exemplary chemotherapy and radiation treatment regimens may be further found, for example, in Bonadonna, G. et al. (1976) N. Engl. J. Med. 294:405-410; Bonadonna, G. et al., in Salmon SE (ed): Adjuvant Therapy of Cancer VI, pp 169-173, 1990; Weiss, R. B. et al. (1987) Am J Med 83:455-463; Budman, D. R. et al. (1992) Proc. Am. Soc. Clin. Oncol. 11:51; Hortobagyi, G. N. et al. (1979) Cancer 43:1225-1233; Fisher, B. et al. (1990) J. Clin. Oncol. 8:1483; Henderson, I. C. et al. (1998) Proc. Am. Soc. Clin. Oncol. 17:101A; Slamon, D. et al. (1998) Proc. Am. Soc. Clin. Oncol. 17:377A; Norton, L. et al. (1999) Proc. Am. Soc. Clin. Oncol. 18:483A; Pouillart, P. et al. (1999) Proc. Am. Soc. Clin. Oncol. 18:2275A; Nabholtz, S. M. et al. (1999) Proc. Am. Clin. Oncol. 18:485A; Seidman, A. D. et al. (2000) Proc. Am. Soc. Clin. Oncol. 19:319A; Seidman, A. D. et al. (1995) J. Clin. Oncol. 13:2575-2581; Ravdin, P. M. et al. (1995) J. Clin. Oncol. 13:2879-2885; Vogel, C. et al. (2000) Proc. Am. Soc. Clin. Oncol. 19:275A; Michaud, L. et al. (2000) Proc. Am. Soc. Clin. Oncol. 19:402A; Leichman, L. et al. (1985) Am. J. Med. 78:211-215; Wagner, J. P. et al. (1994) Int. J. Radiat. Oncol. Biol. Phys. 29:17-23; Poon, M. A. et al. (1989) J. Clin. Oncol. 7:1407-1418; Moertel, C. G. et al. (1995) Ann. Intern. Med. 122:321-326; Moertel, C. G. et al. (1990) N. Engl. J. Med. 322:352-358; Wolnark, N. et al. (1996) Proc. Am. Soc. Clin. Oncol. 15:205; Moertel, C. G. et al. (1994) J. Clin. Oncol. 12:21-27; Saltz, L. B. et al. (1999) Proc. Am. Soc. Clin. Oncol. 18:898A; Saltz, L. B. et al. (2000) N. Engl. J. Med. 343:905?14; Pitot, H. C. et al. (1997) J. Clin. Oncol. 15:2910-2919; Cunningham, D. et al. (1998) Proc. Am. Soc. Clin. Oncol. 17:1A; Twelves, C. et al. (1999) Proc. Am. Soc. Clin. Oncol. 18:1010A; Herskovic, A. et al. (1992) N. Engl. J. Med. 326:1593-1598; Preusser, P. et al. (1989) J. Clin. Oncol. 7:1310-1317; Lemer, A. et al. (1992) J. Clin. Oncol. 10:536-540; Kelsen, D. et al. (1992) J. Clin. Oncol. 10:541-548; Macdonald, J. S. et al. (2000) Proc. Am. Soc. Clin. Oncol. 19:1A; Gastrointestinal Tumor Study Group (1987) Cancer 59:2006-2010; Moertel, C. G. et al. (1994) J. Clin. Oncol. 12:21-27; Burris, H. A. et al. (1997) J. Clin. Oncol. 15:2403-2413; Sternberg, J. J. et al. (1977) JAMA 238:2282-2287; Loehrer, P. J. et al. (1992) J. Clin. Oncol. 10:1066-1073; Redman, B. et al. (1997) Proc. Am. Soc Clin. Oncol. 16:325A; Kaufman, D. et al. (1998) Proc Am. Soc. Clin. Oncol. 17:320A; Burch, P. A. et al. (1999) Proc. Am. Soc. Clin. Oncol. 18:1266A; Vaishampayan, U. et al. (1999) Proc. Am. Soc. Clin Oncol. 18:1282A; Pienta, K. J. et al. (1994) J. Clin. Oncol. 12:2005-2012; Tannock, I. F. et al. (1996) J. Clin.

Oncol. 14:1756-1764; Crawford, E. D. et al. (1987) N. Engl. J. Med. 32:419-424; Jurincic, C. D. et al. (1991) Semin. Oncol. 18 (suppl 6): 21-25; Fyfe, G. et al. (1995) J. Clin. Oncol. 13:688-696; Yang, J. C. et al. (1998) J. Clin. Oncol. 12:1572-1576; Williams, S. D. et al. (1987) N. Engl. J. Med. 316:1435-1440; Loehrer, P. J. et al. (1988) Ann. Intern. Med. 109:540-546; Miller, K. D. et al. (1997) J. Clin. Oncol. 15:1427-1431; Loehrer, P. J. et al. (1988) Ann. Intern. Med. 109:540-546; Murad, A. M. et al. (1992) Proc. Am Soc Clin Oncol 11:229; Morris, M. et al. (1999) N. Engl. J. Med 340:1137-1143; Rose, P. G. et al. (1999) N. Engl. J. Med. 340:1144-1153; Albert, D. et al. (1992) J. Clin. Oncol. 10:706-717; McGuire, W. P. et al. (1996) N Engl J Med 334:1-6; Coleman, R. L. et al. (1997) Cancer J. Sci. Am. 3:246-253; Iva, B. et al. (2000) Proc. Am. Soc. Clin. Oncol. 19:1570A; Muggia, F. M. et al. (1997) J. Clin. Oncol. 15:987-993; Jacobs, C. et al. (1992) J. Clin. Oncol. 10:257-263; Dang, T. P. et al. (1998) Proc. Am. Soc. Clin. Oncol. 17:393a; Roa, V. et al. (1996) Proc. Am. Soc. Clin. Oncol. 15:A1231; Wozniak, A. J. et al. (1998) J. Clin. Oncol. 16:2459-2465; Longeval, E. and Klastersky, J. (1982) Cancer 50:2751-2756; Sandler, A. et al. (1998) Proc. Am. Soc. Clin. Oncol. 17:454A; Ricci, S. et al. (1999) Proc. Am. Soc. Clin. Oncol. 18:480A; Le Chevalier, T. et al. (1994) J. Clin. Oncol. 12:360-367; Shephaerd, F. A. et al. (2000) J. Clin. Oncol. 18:2095-2103; Vansteenkiste, J. et al. (2000) Proc. Am. Soc. Clin. Oncol. 19:1910A; Shin, D. M. et al. (1998) Ann. Intern. Med. 129:100-104; Skarlos, D. V. et al. (1994) Ann. Oncol. 5:601-607; Rosen, G. et al. (1983) J. Cancer Res. Clin. Oncol. 106:55-67; Pratt, C. B. et al. (1985) Cancer 56:1930-1933; Rosen, G. et al. (1981) Cancer 47:2204-2213; Pinedo, H. M. et al. (1984) Cancer 53:182-183; Elias, A. et al. (1989) J. Clin. Oncol. 7:1208-1216; Creagan, E. T. et al. (1999) J. Clin. Oncol. 17:1884-1890; Capizzi, R. L. (1999) Semin. Oncol. 26 (suppl 7): 1-2; Perry, M. C. (1992) Semin. Oncol. 19(5): 453-7, 551-65; Wadler, S et al. (1998) J. Clin. Oncol. 16(9): 3169-78, 1998; all of which are incorporated herein by reference.

The methods of the invention are intended to be used for any type of tumor, cancer, and/or neoplasm, including, but not limited to, those derived from colon, lung, brain, skin, ovary, pancreas, liver, stomach, bladder, bone, testicle, uterus, adipose tissue, throat, kidney, tongue, pituitary gland, thyroid, lymphoid tissue, eye, and/or cervix. Additionally, the methods of the invention are intended to be used for tumors which may be a mixture of more than one cell type.

Although methods of tumor suppression are exemplified in the discussion below, it is understood that the alternative methods described above are equally applicable and suitable, and that the endpoints of these methods (e.g., efficacy of treatment) are measured using methods standard in the art, including the diagnostic and assessment methods described above.

III. Screening Assays

The invention provides a method (also referred to herein as a "screening assay") for identifying modulators, i.e., candidate or test compounds or agents (e.g., peptides, peptidomimetics, small molecules or other drugs) which are capable of reducing, preventing, and/or inhibiting metastasis of tumor cells.

In one embodiment, the invention provides assays for screening candidate or test compounds which bind to or modulate the activity or production of $Gb_3$ in a cell. In another embodiment, the invention provides methods for screening candidate or test compounds which inhibit or downregulate production of $Gb_3$, or of any enzyme in the $Gb_3$ synthesis pathway (e.g., α1,4-galacosyltransferase, also known as $Gb_3$ synthase). The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:45).

Examples of methods for the synthesis of molecular libraries can be found in the art, for example, in: DeWitt et al. (1993) Proc. Natl. Acad. USA 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc. Natl. Acad. Sci. USA 89:1865-1869) or on phage (Scott and Smith (1990) Science 249:386-390); (Devlin (1990) Science 249:404-406); (Cwirla et al. (1990) Proc. Natl. Acad. Sci. USA 87:6378-6382); (Felici (1991) J. Mol. Biol. 222:301-310); (Ladner supra.).

In one embodiment, an assay is a cell-based assay in which a cell which produces Gb3 (e.g., a tumor cell) is contacted with a test compound and the ability of the test compound to modulate Gb3 production or activity is determined. Determining the ability of the test compound to modulate Gb3 activity or production can be accomplished by monitoring, for example, filopodia formation and/or invasiveness of the cell. Methods for determining the ability of the test compound to modulate filopodia formation and/or invasiveness are known in the art, and are also described herein in the Examples section. Also see the publicly available site on the world wide web cancer.gov/faculties/mwg/resources/MetastasisMethods.asp and Metastasis Research Protocols, Volume 1; Ed, Susan A. Brooks; Humana Press (2001).

The ability of the test compound to bind to $Gb_3$ can also be determined. Determining the ability of the test compound to bind to $Gb_3$ can be accomplished, for example, by coupling the compound with a radioisotope or enzymatic label such that binding of the compound to $Gb_3$ can be determined by detecting the labeled compound in a complex. Alternatively, $Gb_3$ could be coupled with a radioisotope or enzymatic label. For example, compounds can be labeled with 125I, 35S, 14C, or 3H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to interact with $Gb_3$ without the labeling of any of the interactants. For example, a microphysiometer can be used to detect the interaction of a compound with $Gb_3$ without the labeling of either the compound or the $Gb_3$. McConnell, H. M. et al. (1992) Science 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and $Gb_3$.

In another embodiment, modulators of $Gb_3$ production are identified in a method wherein a cell is contacted with a candidate compound and the production of $Gb_3$ in the cell is determined. The level of production of $Gb_3$ in the presence of the candidate compound is compared to the level of production of $Gb_3$ in the absence of the candidate compound. The candidate compound can then be identified as a modulator of $Gb_3$ production based on this comparison. For example, when production of $Gb_3$ is greater (statistically significantly greater) in the presence of the candidate compound than in its absence, the candidate compound is identified as a stimulator of production. Alternatively, when production of $Gb_3$ is less (statistically significantly less) in the presence of the candidate compound than in its absence, the candidate compound is identified as an inhibitor of $Gb_3$ production. The level of $Gb_3$ production in the cells can be determined by methods described herein for detecting Gb3. For example, $Gb_3$ may be detected using anti-$Gb_3$ antibodies or labeled Stx1B or labeled Stx2B. In another embodiment, modulators of $Gb_3$ production may be identified based on the ability to modulate expression or activity of enzymes in the $Gb_3$ synthesis pathway.

In another aspect, the invention pertains to a combination of two or more of the assays described herein. For example, a modulating agent can be identified using a cell-based or a cell-free assay, and the ability of the agent to modulate tumor metasasis or invasivesness can be confirmed in vivo, e.g., in an animal such as an animal model for cellular transformation or tumorigenesis.

This invention further pertains to novel agents identified by the above-described screening assays. Accordingly, it is within the scope of this invention to further use an agent identified as described herein in an appropriate animal model (e.g., an animal model such as any of those described above). For example, an agent identified as described herein (e.g., a $Gb_3$ modulating agent) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

In another aspect, cell-based systems, as described herein, may be used to identify compounds which may act to ameliorate tumor metastasis and/or invasiveness. For example, such cell systems may be exposed to a compound, suspected of exhibiting an ability to ameliorate tumor metastasis and/or invasiveness, at a sufficient concentration and for a time sufficient to elicit such an amelioration of tumor metastasis and/or invasiveness in the exposed cells. After exposure, the cells are examined to determine whether one or more of the tumor metastasis and/or invasiveness cellular phenotypes has been altered to resemble a more normal or more wild type, non-metastatic disease phenotype (e.g., a reduction in the amount of filopodia).

IV. Diagnostic Assays

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining $Gb_3$ production as well as $Gb_3$ activity, in the context of a biological sample (e.g., cells and/or tissue) to thereby determine whether tumor cells (e.g., tumor cells in an individual subject) are capable of or at risk of metastasizing. For example, $Gb_3$ production in tumor cells can be assayed in a biological sample. Such assays can be used for prognostic or predictive purpose to thereby prophylactically treat an individual prior to the onset of metasasis.

An exemplary method for detecting the presence or absence of $Gb_3$ in a biological sample involves obtaining a biological sample from a test subject and contacting the biological sample with a compound or an agent capable of detecting $Gb_3$, such that the presence of $Gb_3$ in the biological sample. A preferred agent for detecting $Gb_3$ is an antibody capable of binding to $Gb_3$, preferably an antibody with a detectable label. Antibodies can be polyclonal, or more preferably, monoclonal. An intact antibody, or a fragment thereof (e.g., Fab or $F(ab')_2$) can be used. Another preferred agent for detecting $Gb_3$ is Stx1B protein with a detectable label. The term "labeled", with regard to the protein or antibody, is intended to encompass direct labeling of the protein or antibody by coupling (i.e., physically linling) a detectable substance to the protein or antibody, as well as indirect labeling of the protein or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect $Gb_3$ in a biological sample in vitro as well as in vivo. For example, in vitro techniques for detection of $Gb_3$ include enzyme linked immunosorbent assays (ELISAs), Western blots, immunoprecipitations and immunofluorescence. Furthermore, in vivo techniques for detection of a $Gb_3$ protein include introducing into a subject a labeled anti-$Gb_3$ antibody. For example, the antibody can be labeled with a radioactive marker whose presence and location in a subject can be detected by standard imaging techniques. Alternatively, Stx1B and/or Stx2B can be labeled or conjugated with any indicator/reporter used in tomography, CAT, PET scans, etc. for direct visualization of $Gb_3$ and identifying the location of potentially invasive and/or metastatic cancer cells due to the accumulation of $Gb_3$ in these cells.

The diagnostic assays described herein can be used to determine whether a subject can be administered an agent (e.g., an antagonist, peptidomimetic, protein, peptide, nucleic acid, small molecule, or other drug candidate) to prevent, downregulate, and/or inhibit metastasis in the subject. For example, such methods can be used to determine whether a subject can be effectively treated with an agent that inhibits metasasis such as Stx1B and/or Stx2B.

In another embodiment, the present invention provides a method for monitoring the effectiveness of treatment of a subject with an agent (e.g., an antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a $Gb_3$ in the preadministration sample; (iii) obtaining one or more post-administration samples from the subject; (iv) detecting the level of expression or activity of the $Gb_3$ in the post-administration samples; (v) comparing the level of expression or activity of the Gb$_3$ in the pre-administration sample with the Gb$_3$ in the post administration sample or samples: and (vi) altering the administration of the agent to the subject accordingly. For example, increased administration of the agent may be desirable to decrease the expression or activity of Gb$_3$, i.e., to increase the effectiveness of the agent. According to such an embodiment, Gb$_3$ expression or activity may be used as an indicator of the effectiveness of an agent, even in the absence of an observable phenotypic response.

V. Isolated Nucleic Acid Molecules Relating to the Beta Subunit of Shiga Toxin

One aspect of the invention pertains to isolated nucleic acid molecules that encode the Shiga toxin, and in particular, the beta subunit (Stx1b and Stx2B) proteins used in the methods of the invention. As used herein, the term 'nucleic acid molecule' is intended generally to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

In general, optimal practice of the present invention can be achieved by use of recognized manipulations. For example, techniques for isolating MRNA, purifying and analyzing nucleic acids, methods for making recombinant vector DNA, cleaving DNA with restriction enzymes, ligating DNA, introducing DNA into host cells by stable or transient means, culturing the host cells, producing recombinant adenoviral vectors, and isolating and purifying polypeptides a are generally known in the field. See generally Sambrook et al., *Molecular Cloning* (2d ed. 1989), and Ausubel et al., *Current Protocols in Molecular Biology*, (1989) John Wiley & Sons, New York.

The term 'isolated nucleic acid molecule' includes nucleic acid molecules which are separated from other nucleic acid molecules which are present in the natural source of the nucleic acid. For example, with regards to genomic DNA, the term 'isolated' includes nucleic acid molecules which are separated from the chromosome with which the genomic DNA is naturally associated. Preferably, an 'isolated' nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecules can contain less than about 5 kb, 4 kb, 3 kb, 2 kb, 1 kb, 0.5 kb or 0.1 kb of nucleotide sequences which naturally flank the nucleic acid molecule in genomic DNA. Moreover, an 'isolated' nucleic acid molecule can be substantially free of other cellular material, or culture medium when produced by recombinant techniques, or substantially free of chemical precursors or other chemicals when chemically synthesized.

A nucleic acid molecule of the present invention, e.g., a nucleic acid molecule encoding Stx1B, or a portion thereof, can be constructed using standard molecular biology techniques and the sequence information provided herein. Moreover, a nucleic acid molecule encoding all or a portion of Stx1B or Stx2B can be isolated by the polymerase chain reaction (PCR) using synthetic oligonucleotide primers designed based upon the sequence Stx1B or Stx2B.

In a preferred embodiment, the nucleic acid molecules used in the methods of the invention are produced by inserting a double-stranded DNA molecule that encodes a protein into an expression vector (e.g., a plasmid vector), such that the protein can be expressed in a cell (e.g., a cancer cell).

A nucleic acid of the invention can be amplified using cDNA, MRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to Stx1B nucleotide sequences can be prepared by standard synthetic techniques, e.g., using an automated DNA synthesizer.

The nucleic acid molecule of the invention can comprise only a portion of the nucleic acid sequence encoding Stx1B, for example, a fragment which can be used as a probe or primer. The probe/primer (e.g., oligonucleotide) typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides, or a complement thereof.

Exemplary probes or primers are at least (or no greater than) 12 or 15, 20 or 25, 30, 35, 40, 45, 50, 55, 60, 65, 70, 75 or more nucleotides in length and/or comprise consecutive nucleotides of an isolated nucleic acid molecule described herein. Also included within the scope of the present invention are probes or primers comprising contiguous or consecutive nucleotides of an isolated nucleic acid molecule described herein, but for the difference of 1, 2, 3, 4, 5, 6, 7, 8, 9 or 10 bases within the probe or primer sequence. In preferred embodiments, the probe further comprises a label group attached thereto, e.g., the label group can be a radioisotope, a fluorescent compound, an enzyme, or an enzyme co-factor. In another embodiment a set of primers is provided, e.g., primers suitable for use in a PCR, which can be used to amplify a selected region of a nucleotide sequence, e.g., a domain, region, site or other sequence described herein. The primers should be at least 5, 10, or 50 base pairs in length and less than 100, or less than 200, base pairs in length. The primers should be identical, or differ by no greater than 1, 2, 3, 4, 5, 6, 7, 8, 9 or 10 bases when compared to a sequence disclosed herein or to the sequence of a naturally occurring variant. Such probes can be used as a part of a diagnostic test kit for identifying cells or tissue which contain the expression construct, or which express the expressible sequence.

In another embodiment, nucleic acid molecules of the invention can comprise variants of the sequence elements disclosed herein. Nucleic acid variants can be naturally occurring, such as allelic variants (same locus), homologues (different locus), and orthologues (different organism, e.g., mouse) or can be non-naturally occurring. Non-naturally occurring variants can be made by mutagenesis techniques, including those applied to polynucleotides, cells, or organisms. The variants can contain nucleotide substitutions, deletions, inversions and insertions. Allelic variants result, for example, from DNA sequence polymorphisms within a population (e.g., the human or bacterial population).

VI. Recombinant Expression Vectors and Host Cells Relating to the Beta Subunit of Shiga Toxin Another aspect of the invention pertains to vectors, for example recombinant expression vectors, containing an Stx1B or Stx2B encoding nucleic acid molecule. As used herein, the term 'vector' refers to a nucleic acid molecule capable of transporting another nucleic acid to which it has been linked. One type of vector is a 'plasmid', which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as 'expression vectors'. In general, expression vectors of utility in recombinant DNA techniques are often in the form of plasmids. In the present specification, 'plasmid' and 'vector' can be used interchangeably as the plasmid is the most commonly used form of vector. However, the invention is intended to include such other forms of expression vectors, such as viral vectors.

Another aspect of the invention pertains to host cells into which the nucleic acid molecules of the invention are introduced, which may or may not containing sequences which allow it to recombine into the host cell's genome. The terms 'host cell' and 'recombinant host cell' are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a vector can be propagated and/or expressed in bacterial cells such as *E. coli*, insect cells, yeast or mammalian cells (such as Chinese hamster ovary cells (CHO), COS cells (e.g., COS7 cells), C6 glioma cells, HEK 293T cells, or neurons). Other suitable host cells are known to those skilled in the art. In a preferred embodiment, a host cell is a human cancer cell (e.g., a colon cancer cell).

Vector DNA can be introduced into prokaryotic or eukaryotic cells via conventional transformation or transfection techniques. As used herein, the terms 'transformation' and 'transfection' are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an siRNA can be introduced on a separate vector. Cells stably transfected with the introduced nucleic acid can be identified by drug selection (e.g., cells that have incorporated the selectable marker gene will survive, while the other cells die).

VII. Isolated Proteins and Antibodies Relating to the Beta Subunit of Shiga Toxin One aspect of the invention pertains to the use of isolated or recombinant Stx1B and Stx2B proteins and polypeptides, and biologically active portions thereof antibodies. In one embodiment, native Stx1B and Stx2B proteins can be isolated from cells or tissue sources by an appropriate purification scheme using standard protein purification techniques. In another embodiment, Stx1B and Stx2B proteins are produced by recombinant DNA techniques. Alternative to recombinant expression, an Stx1B or Stx2B protein or polypeptide can be synthesized chemically using standard peptide synthesis techniques.

An "isolated" or "purified" protein or biologically active portion thereof is substantially free of cellular material or other contaminating proteins from the cell or tissue source from which the Stx1B or Stx2B protein is derived, or substantially free from chemical precursors or other chemicals when chemically synthesized. The language "substantially free of cellular material" includes preparations of Stx1B or Stx2B protein in which the protein is separated from cellular components of the cells from which it is isolated or recombinantly produced, In one embodiment, the language "substantially free of cellular material" includes preparations of Stx1B or Stx2B protein having less than about 30% (by dry weight) of non-Stx1B or Stx2B protein (also referred to herein as a "contaminating protein"), more preferably less than about 20% of non-Stx1B or Stx2B protein, still more preferably less than about 10% of non-Stx1B or Stx2B protein, and most preferably less than about 5% non-Stx1B or Stx2B protein. When the Stx1B or Stx2B protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of Stx1B or Stx2B protein in which the protein is separated from chemical precursors or other chemicals which are involved in the synthesis of the protein. In one embodiment, the language "substantially free of chemical precursors or other chemicals" includes preparations of Stx1B or Stx2B protein having less than about 30% (by dry weight) of chemical precursors or non-Stx1B or Stx2B chemicals, more preferably less than about 20% chemical precursors or non-Stx1B or Stx2B chemicals, still more preferably less than about 10% chemical precursors or non-Stx1B or Stx2B chemicals, and most preferably less than about 5% chemical precursors or non-Stx1B or Stx2B chemicals.

As used herein, a "biologically active portion" of a Stx1B or Stx2B protein includes a fragment of a Stx1B or Stx2B protein which participates in an interaction between a Stx1B or Stx2B molecule and a non-Stx1B or Stx2B molecule (e.g., $Gb_3$). Biologically active portions of a Stx1B or Stx2B protein include peptides comprising amino acid sequences sufficiently homologous or identical to or derived from the Stx1B or Stx2B amino acid sequences, e.g., the amino acid sequences described herein, which include sufficient amino acid residues to exhibit at least one activity of a $Gb_3$ lipid. Typically, biologically active portions comprise a domain or motif with at least one activity of the Stx1B or Stx2B protein, e.g., the ability to interact with $Gb_3$, and/or the ability to induce apoptosis in a tumor cell (e.g., a metastatic tumor cell). Biologically active portions of a Stx1B or Stx2B protein can be used as targets for developing agents which modulate a Stx1B or Stx2B mediated activity, e.g., any of the aforementioned Stx1B or Stx2B activities.

The methods of the invention include the use both Stx1B and Stx2B proteins, polypeptides, and peptides, as well as Stx1B and Stx2B conjugates. While Stx1B or Stx2B protein alone can induce cell death in a tumor cell that expresses $Gb_3$, Stx1B or Stx2B can also be used as a delivery vehicle to deliver a therapeutic agent (e.g., a cytoxic agent) to a tumor cell that produces $Gb_3$. As used herein, an "Stx1B or Stx2Bconjugate" includes a biologically active portion of an Stx1B or Stx2B peptide operatively linked to a therapeutic agent. As used herein, a "therapeutic agent" includes any agent that, when applied to, expressed or injected in, or contacted with a cell, has a therapeutic effect on the cell. Preferably, a "therapeutic effect" includes, but is not limited to, inhibition and/or reduction of metastasis and/or invasion, as well as induction of cell death. It will be understood that the Stx1B and Stx2B proteins, polypeptides, peptides, and respective conjugates may comprise naturally-occurring amino acids, and/or may be modified as described below.

As used herein, the terms "peptide", "peptide compound" and "peptidic structure" are intended to include peptides comprised of naturally-occurring L-amino acids, as well as peptide derivatives, peptide analogues and peptide mimetics of the naturally-occurring L-amino acid structures. The terms "peptide analogue", "peptide derivative" and "peptidomimetic" as used herein are intended to include molecules which mimic the chemical structure of a peptide and retain the functional properties of the peptide (e.g., the ability to bind PSMA or a PSMA expressing cell). Approaches to designing peptide analogues, derivatives and mimetics are known in the art. For example, see Farmer, P. S. in Drug Design (E. J. Ariens, ed.) Academic Press, New York, 1980, vol. 10, pp. 119-143; Ball. J. B. and Alewood, P. F. (1990) J. Mol. Recognition 3:55; Morgan, B. A. and Gainor, J. A. (1989) Ann. Rep. Med. Chem. 24:243; and Freidinger, R. M. (1989) Trends Pharmacol. Sci. 10:270. As used herein, a "derivative" of a compound X (e.g., a peptide or amino acid) refers to a form of X in which one or more reaction groups on the compound have been derivatized with a substituent group. Examples of peptide derivatives include peptides in which an amino acid side chain, the peptide backbone, or the amino- or carboxy-terminus has been derivatized (e.g., peptidic compounds with methylated amide linkages).

As used herein an "analogue" of a compound X (e.g., a peptide or amino acid) refers to a compound which retains chemical structures of X necessary for functional activity of X yet which also contains certain chemical structures which differ from X. An example of an analogue of a naturally-occurring peptide is a peptides which includes one or more non-naturally-occurring amino acids. As used herein, a "mimetic" of a compound X refers to a compound in which chemical structures of X necessary for functional activity of X have been replaced with other chemical structures which mimic the conformation of X. Examples of peptidomimetics include peptidic compounds in which the peptide backbone is substituted (see e.g., James, G. L. et al. (1993) Science 260: 1937-1942), peptides in which all L-amino acids are substituted with the corresponding D-amino acids and "retro-inverso" peptides (see U.S. Pat. No. 4,522,752 by Sisto), described further below.

The term mimetic, and in particular, peptidomimetic, is intended to include isosteres. The term "isostere" as used herein is intended to include a chemical structure that can be substituted for a second chemical structure because the steric conformation of the first structure fits a binding site specific for the second structure. The term specifically includes peptide back-bone modifications (i.e., amide bond mimetics) well known to those skilled in the art. Such modifications include modifications of the amide nitrogen, the a-carbon, amide carbonyl, complete replacement of the amide bond, extensions, deletions or backbone crosslinks. Several peptide backbone modifications are known, including j[CH2S], j[CH2NH], j[CSNH2], j[NHCO], j[COCH2], and j[(E) or (Z) CH=CH]. In the nomenclature used above, j indicates the absence of an amide bond. The structure that replaces the amide group is specified within the brackets (see e.g., James, G. L. et al. (1993) Science 260:1937-1942).

Other possible modifications include an N-alkyl (or aryl) substitution (j[CONR]), backbone crosslinking to construct lactams and other cyclic structures, substitution of all D-amino acids for all L-amino acids within the compound ("inverso" compounds) or retro-inverso amino acid incorporation (j[NHCO]). By "inverso" is meant replacing L-amino acids of a sequence with D-amino acids, and by "retro-inverso" or "enantio-retro" is meant reversing the sequence of the amino acids ("retro") and replacing the L-amino acids with D-amino acids. For example, if the parent peptide is Thr-Ala-Tyr, the retro modified form is Tyr-Ala-Thr, the inverso form is thr-ala-tyr, and the retro-inverso form is tyr-ala-thr (lower case letters refer to D-amino acids). Compared to the parent peptide, a retro-inverso peptide has a reversed backbone while retaining substantially the original spatial conformation of the side chains, resulting in a retro-inverso isomer with a topology that closely resembles the parent peptide. See Goodman et al. "Perspectives in Peptide Chemistry" pp. 283-294 (1981). See also U.S. Pat. No. 4,522,752 by Sisto for further description of "retro-inverso" peptides. Other derivatives include C-terminal hydroxymethyl derivatives, O-modified derivatives (e.g., C-terminal hydroxymethyl benzyl ether) and N-terminally modified derivatives including substituted amides such as alkylamides and hydrazides.

As used herein, the term "amino acid structure" (such as a "leucine structure", a "phenylalanine structure" or a "glutamine structure") is intended to include the amino acid, as well as analogues, derivatives and mimetics of the amino acid that maintain the functional activity of the compound (e.g., the ability to bind $Gb_3$ or to $Gb_3$ producing cells). For example, the term "phenylalanine structure" is intended to include phenylalanine as well as pyridylalanine and homophenylalanine. The term "leucine structure" is intended to include leucine, as well as substitution with valine or other natural or non-natural amino acid having an aliphatic side chain, such as norleucine.

The amino- and/or carboxy-terminus of the peptide compounds of the invention can be unmodified hydrogen. Alternatively, the amino- and/or carboxy-terminus of the peptide compound can be modified with a derivative group. Amino-derivative groups which can be present at the N-terminus of a peptide compound include acetyl, aryl, aralkyl, acyl, epoxysuccinyl and cholesteryl groups. Carboxy-derivative groups which can be present at the C-terminus of a peptide compound include alcohol, aldehyde, epoxysuccinate, acid halide, carbonyl, halomethane, and diazomethane groups.

The peptide compounds used in the methods of the invention can be prepared by standard peptide synthesis methods known in the art. The peptide compounds used in the methods of the invention can also be prepared by preparing nucleic acid molecules that encode the peptides, and expressing the encoded peptides using standard molecular biology methods known in the art. The ability of a peptide compound of the invention to bind to an $Gb_3$ or $Gb_3$ producing cells can be evaluated using binding assays. The ability of a peptide compound of the invention to modulate Gb3 activity can be evaluated using an assay that measures $Gb_3$ activity (e.g., an invasion assay).

The peptide compounds of the invention may be coupled to other molecules for use in the therapeutic and/or diagnostic methods of the invention. For example, the peptide compounds may be linked other peptides, e.g., carrier peptides, or to molecules which are used for diagnostic and/or therapeutic methods. For example, the peptide compounds of the invention can be used diagnostically to monitor $Gb_3$ production and expression on tumor cell membranes, or to measure the number of metastasized cells. Detection can be facilitated by coupling (i.e., physically linking) the peptide to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, b-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S, 32P, 33P, and 3H.

The peptides of the invention may also be coupled to conjugated to a therapeutic moiety such as a cytotoxin, a therapeutic agent or a radioactive metal ion. A cytotoxin or cytotoxic agent includes any agent that is detrimental and/or toxic to cells. Examples include, but are not limited to, diphtheria toxin (e.g., diphtheria toxin A), Pseudomonas exdotoxin A, taxol, cytochalasin B, gramicidin D, ethidium bromide, emetine, mitomycin, etoposide, tenoposide, vincristine, vinblastine, colchicine, doxorubicin, daunorubicin, dihydroxy anthracene-dione, mitoxantrone, mithramycin, actinomycin D, dihydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The invention also provides chimeric or fusion proteins of the peptide compounds described herein. As used herein, a "chimeric protein" or "fusion protein" comprises peptides (e.g., Stx1B and Stx2B peptides) of the invention operatively linked to heterologous peptide sequences. "Heterologous peptide sequences” includes a peptide or polypeptide having an amino acid sequence corresponding to a protein which is not substantially homologous to peptide compound of the invention. Within the fusion protein, the term “operatively linked” is intended to indicate that the peptide of the invention and the heterologous peptide sequences are fused in-frame to each other. The heterologous peptide sequences can be fused to the N-terminus or C-terminus of the peptide of the invention.

Preferably, a chimeric or fusion protein of the invention is produced by standard recombinant DNA techniques. For example, DNA fragments coding for the different peptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). A peptide-encoding nucleic acid can be cloned into such an expression vector such that the fusion moiety is linked in-frame to the peptide.

VIII. Pharmaceutical Compositions

Another aspect of the invention pertains to pharmaceutical compositions of the compounds of the invention. The pharmaceutical compositions of the invention typically comprise a compound of the invention and a pharmaceutically acceptable carrier. As used herein “pharmaceutically acceptable carrier” includes any and all solvents, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Depending on the route of administration, the compound may be coated in a material to protect it from the action of enzymes, acids and other natural conditions which may inactivate the agent. For example, the compound can be administered to a subject in an appropriate carrier or diluent co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluoro-phosphate (DEP) and trasylol. Liposomes include water-in-oil-in-water emulsions as well as conventional liposomes (Strejan, et al., (1984) J. Neuroimmunol 7:27). Dispersions can also be prepared in glycerol, liquid polyethylene glycols, and mixtures thereof and in oils. Under ordinary conditions of storage and use, these preparations may contain a preservative to prevent the growth of microorganisms.

The active agent in the composition (i.e., a peptide compound of the invention) preferably is formulated in the composition in a therapeutically effective amount. A "therapeutically effective amount" refers to an amount effective, at dosages and for periods of time necessary, to achieve the desired therapeutic result to thereby influence the therapeutic course of a particular disease state. A therapeutically effective amount of an active agent may vary according to factors such as the disease state, age, sex, and weight of the individual, and the ability of the agent to elicit a desired response in the individual. Dosage regimens may be adjusted to provide the optimum therapeutic response. A therapeutically effective amount is also one in which any toxic or detrimental effects of the agent are outweighed by the therapeutically beneficial effects. In another embodiment, the active agent is formulated in the composition in a prophylactically effective amount. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The amount of active compound in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce each the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

A compound of the invention can be formulated into a pharmaceutical composition wherein the compound is the only active agent therein. Alternatively, the pharmaceutical composition can contain additional active agents. For example, two or more peptide compounds of the invention may be used in combination. Moreover, a peptide compound of the invention can be combined with one or more other agents that have modulatory effects on $Gb_3$ activity or on cancer cells.

This invention is further illustrated by the following examples which should not be construed as limiting. The contents of all references, patents, and published patent applications cited throughout this application, as well as the figures, are incorporated herein by reference.

EXAMPLES

Materials and Methods

The following materials and methods were used in Examples 1-10 unless otherwise noted.

Cell Culture and Chemicals

The following cell lines were obtained from the American Type Culture Collection (ATCC, Mannassas, Va.): Caco-2, IEC6, CHO, T84, OK and HT-29. Primary antibodies used were raised against the following proteins: $\beta$-catenin, $\alpha$-tubulin and $\beta$-tubulin (Sigma, St. Louis, Mo.), $Gb_3$ (Seikagaku America, Falmouth, Mass.). Dilutions were according to the manufacturer's recommendations. Alexa 568-conjugated secondary antibodies and phalloidin and Cyto7 fluorescent dye were from Molecular Probes (Eugene, Oreg.). PPMP was from Biomol (Plymouth Meeting, Pa.). TRITC-labeled cholera toxin B-subunit (CTB) was from List Biological Laboratories, Inc. (Campbell, Cailf.). Recombinant B subunit of Shiga toxin (Stx1B) was obtained from the GRASP Center, New England Medical Center. For fluorescence microcopy experiments, Stx1B was conjugated with Oregon Green 488 fluorescent dye (Molecular Probes) according to the manufacturer's recommendations.

Fluorescence Microscopy

To evaluate the distribution of $Gb_3$, and $G_{M1}$, cells were incubated for one hour with 0.5 μg/ml Stx1B-Oregon Green 488 (Stx1B-OrG) or 1 μg/ml CTB-TRITC respectively, and free fluorescent toxins were then washed away. All experiments except immunofluorescence were performed on living cells mounted in a perfusion chamber (Warner Instruments, Hamden, Conn.) with HEPES buffer, pH 7.4 at 37° C. on the microscope stage.

For immunofluorescence, surgically removed human colon and liver tissue from archival samples and cells were fixed in 4% formaldehyde in PBS for 10-30 minuntes at 4° C., washed extensively in PBS, incubated with primary antibodies at room temperature for one hour, washed three times in PBS, and incubated with secondary fluorescent antibodies for an additional hour, washed again and mounted on glass slides for confocal microscopy examination.

Microscopy of fixed tissue and living or fixed cells was performed using a multiphoton laser scanning confocal imaging system (MRC-1024; BioRad, Hercules, Calif.) connected to mode-locked Ti:sapphire laser (Tsunami; Spectra-Physics, Mountain View, Calif.). Collected images of confocal optical sectioning with 0.5 μm steps were stored on disc, and fluorescence intensity was analyzed by MetaMorph software (Universal Imaging, Downingtown, Pa.) as described in Kovbasnjuk, O. N. et al. ((2001) *J. Cell Sci.* 114:1425-1430).

Chemoinvasive Assay

Chemoinvasion was assayed in cell-culture chambers using 24-mm Transwell inserts with 8 μm pore membranes (Corning Inc., Fountain Valley, Calif.) as described in Saiki, I. et al. ((1990) *Cancer Res.* 50:3631-3637). The bottom of membranes were pre-coated with laminin (1 μg/ml). Caco-2 cancer cells or OK cells were seeded on the top surface of the filters. After incubation for 24, 48 or 72 hours, cells on both sides of the membrane were stained, and 0.5 μm confocal optical sections using 100× objective lens were taken through the whole membrane thickness. The distribution of cells on the top and bottom surfaces of the membrane and numbers of cells were analyzed using MetaMorph and Volocity (Improvision Inc., Lexington, Mass.) image processing software by image deconvolution and 3D-reconstruction functions. Five fields were examined per membrane.

$Gb_3$-Synthase Transfection

The cDNA encoding human $Gb_3$ synthase was subcloned into the pcDNA3.1 vector. For transient expression of $Gb_3$ synthase into OK cells, cells were seeded at 75-80% confluence onto Transwell filters in 6-well plates 24 hours prior to transfection and transfected with 1 μg of pcDNA3.1/$Gb_3$ using LipofectAmine 2000, using methods recommended by the manufacturer (Invitrogen, Carlsbad, Calif.). After six hours of incubation with the DNA-lipid complexes, the cells were re-fed with serum-containing DMEM/F12 medium. Cells were studied 24, 48 and 72 hours after transfection.

Identification of Proteins Complexed with $Gb_3$ in Caco-2 Cells with a Migratory Phenotype 70% confluent Caco-2 cells grown in 10 cm Petri dishes were vigorously shaken to separate filopodia from cell bodies. Filopodia and cell bodies were collected separately in 1 ml HEPES buffer and homogenized with sonication. The purity of the filopodia fraction was checked under the microscope by labeling of 5 μl of filopodia preparation with Stx1B-OrG, and no cell bodies were detected. The cell fraction homogenate was centrifuged at 3000 g to remove cell debris and nuclei, and then both filopodia and cell preparations were centrifuged at 150,000 g to collect the total membranes. The membranes were lysed with 1% Triton X-100 in HEPES buffer for 30 minutes at 4° C., and centrifuged at 150,000 g for 40 minutes. The detergent-soluble supernatant is referred to herein as "DS". The detergent-insoluble (referred to herein as "DIM") pellet was further solubilized in RIPA buffer. Because the majority of $Gb_3$ resides in LR, the DIM was used as the starting material for identifying $Gb_3$-interacting proteins. Two identical aliquots of proteins from the DS and DIM fractions from both filopodia and cell preparations were separated on SDS-PAGE, one part of which was stained with Coomassie Blue to visualize the isolated proteins, and a second identical part was used for Western blotting analysis. For the Western analysis, anti-$Gb_3$ mAb was used to detect which fractions contained $Gb_3$-positive protein bands, as described in Katagiri, Y. U. et al. ((1999) *J. Biol. Chem.* 274:35278-35282). $Gb_3$-positive bands correspond to $Gb_3$-associated and/or $Gb_3$-binding proteins.

MASS Spectroscopy Analysis

For MASS spectroscopy (MS), protein bands associated with Gb3 were cut from the gel, destained, and then extracted with trypsin (modified; Promega, Madison, Wis.) as described. The resulting extract solutions were frozen and lyophilized to reduce their volume to 15 ml. 5 ml injections were performed on a Hewlett Packard 1100 HPLC, with a Beta Basic-18 capillary column. The eluent was run directly into a Finnigan LCQ at a flow rate of 1 ml/min. The LCQ was set to scan the mass range of 450-800, and the two most intense peaks were selected for ms/ms analysis. Dynamic exclusion was used to allow as many peaks as possible to undergo ms/ms analysis.

Statistics

Data are presented as mean±s.e.m. Significance was determined using the Student's t test, and P values less than 0.05 were considered statistically significant.

Example 1

$Gb_3$ is Present in Metastatic Colon Cancer Tissue

Immunofluorescence staining was performed on five primary human colon cancer tissue samples (Duke's stage D) and two samples of liver metastasis with an antibody against $Gb_3$ or with Stx1B-OrG, which binds specifically to $Gb_3$ (Ling, H. et al. (1998) *Biochemistry* 37:1777-1788). High levels of $Gb_3$ were expressed in both primary tumor and in the liver metastasis (FIGS. 1A and 1C). In contrast, examination of human tissue samples from non-cancer colon tubular adenomas and normal liver demonstrated complete absence of $Gb_3$ or only trace amount of this GSL in colonic epithelial cells and hepatocytes (FIGS. 1B and 1D). Quantitation of $Gb_3$ amount (see Table 1) in metastatic colon cancer tissue samples showed that $Gb_3$ is upregulated ~500% compared to the amount in tubular adenomas, normalized as 100%.

TABLE 1

Amount of $Gb_3$ (in %) in human tissue samples

| Primary metastatic colon cancer | Non-cancer adenoma | Colon cancer metastases into liver | Normal liver |
|---|---|---|---|
| 484 ± 14 | 100 ± 25 | 537 ± 38 | 100 ± 17 |

The amount of Gb3 in normal tissue was calculated from analysis of 8-bit fluorescence images as an average of fluorescence intensity per sample and presented as 100% ± SE. The amount of Gb3 in cancer tissue was calculated similarly and expressed in % relatively to control.

As shown on FIG. 1B, $Gb_3$ is virtually absent in colonic epithelial cells and is expressed in that tissue mostly in red blood cells. Similarly, $Gb_3$ expression in liver metastases was elevated more that 500% compared to normal human liver. This significant $Gb_3$ elevation in the primary colonic tumors and in the colon cancer metastases into the liver of $Gb_3$ suggested a potential role in the development of tumor invasiveness.

Example 2

Anaysis of $Gb_3$ Expressuon in Human Colon Cancer Cell Lines

Several epithelial human colon cancer cell lines including Caco-2, T-84 and HT-29 were examined by immunofluorescence microscopy and FACS for the presence of $Gb_3$-expressing cells. When the cells were 50-70% confluent, two subpopulations of cells were detected in each cell line: one without or with trace amounts of $Gb_3$ and another with a high amount of $Gb_3$, as in the case of primary and metastatic colon cancer tissues. The percent of $Gb_3$-expressing cells was different in the three type of cells with only ~10% of $Gb_3$-containing T-84 cells, ~50% of $Gb_3$-containing Caco-2 cells and virtually all HT-29 cells.

Figure 2:
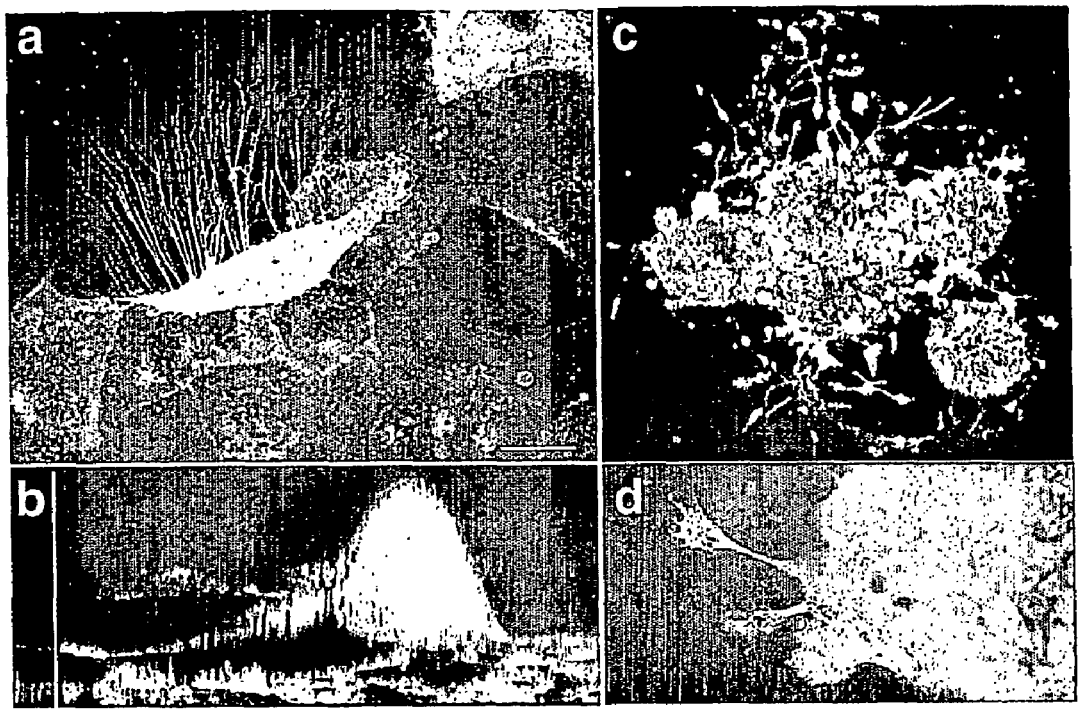
FIGS. 2A-2D depict filopodia-containing cells on the leading edge of a living colon carcinoma monolayer detected by glycosphingolipid $Gb_3$.

In 50-70% confluent monolayers of all three types of the cells, $Gb_3$-containing cells were mostly concentrated at the leading edge of cell islands. Moreover, cells enriched in $Gb_3$ demonstrated a migratory phenotype and form filopodia (FIGS. 2A, 2C, and 2D). In the case of Caco-2 cells (FIG. 2A), the filopodia were very thin (~0.2-0.5 μm), variable in size, in some cases exceeding up to 2-10× the epithelial cell diameter, and were projected in the direction of monolayer growth and cell spreading. In all three cell lines there was a strong correlation between the amount of $Gb_3$ and the appearance of filopodia. Cells that form filopodia were significantly enriched in $Gb_3$ compared to neighboring cells without filopodia from the same leading edge (FIGS. 2A and 2D). Quantitative analysis of fluorescence intensity of 11 Caco-2 cells with and without filopodia showed that cells with filopodia express at least 3-5 times more $Gb_3$ than cells without them, and the average pixel intensity was 238±18 grey levels (g.l.) in filopodia-containing cells vs. 52±10 g.l. in cells without filopodia, $p<0.05$. The filopodia-containing cells also have larger cell bodies than cells without filopodia from the same leading edge (FIG. 2B). Measurement of the height of 20 filopodia-containing cells showed that they were ~3 times taller than non-filopodia containing cells (33±6 μm vs 7±2 μm, $p<0.05$).

To test whether $Gb_3$-expressing cells with filopodia were characteristic features of epithelial colon cancer cells, several non-cancerous epithelial cell lines were tested for the presence of $Gb_3$-containing cells and for appearance of $Gb_3$-containing filopodia. The non-cancer cell lines tested, which include polarized epithelial OK cells (derived from kidney proximal tubule), CHO cells, and IEC-6 cells (non-polarized rat intestinal epithelial crypt cells), did not contain $Gb_3$-enriched cells with filopodia on the leading edge of growing monolayers.

Example 3

$Gb_3$ Expression and Cell Invasiveness

The appearance of cells with filopodia is consistent with their involvement in cell spreading, migration, or invasiveness. Because $Gb_3$-enriched filopodia-containing cells were not detected in non-cancerous cells, and because epithelial cells with high amounts of $Gb_3$ were a feature of metastatic tissue samples, is suggested that these cells with a migratory phenotype might represent an invasive pool. To test this hypothesis, a standardized chemoinvasive assay (Saiki, I. et al. (1990) *Cancer Res.* 50:3631-3637), which correlates with metastatic ability in vivo (Muller, A. et al. (2001) *Nature* 410:50-56) was performed using Caco-2 cells. This demonstrated that only filopodia-containing $Gb_3$-enriched cells migrate to the bottom surface of the filter by the penetration of filopodia through the filter pores (FIGS. 3A-3D), despite the fact that the filopodia-containing cells were several times larger (FIG. 2B) than cells without filopodia.

Filopodia-containing cells, which migrated through the filter, then created a confluent monolayer of cells. The attempt to clone the $Gb_3$-containing Caco-2 cell population resulted in formation of a cell monolayer with only ~50% $Gb_3$-Containing cells, similar to wild type Caco-2 monolayers. This indicates that the invasive sub-population of cells does not represent a separate clone, but rather appears due to regulation of gene, protein and/or lipid expression by unknown signal transduction mechanisms.

Example 4

$Gb_3$ is Sufficient for the Invasive Phenotype

To test whether $Gb_3$ expression is sufficient for epithelial cells to invade, OK cells, which do not express endogeneous $Gb_3$ (FIG. 3E) and are not invasive (FIG. 3F) were transiently transfected with a cDNA encoding $Gb_3$ synthase (Keusch, J. J et al. (2000) *J. Biol. Chem.* 275:25315-21; Steffensen, R. et al. (2000) *J. Biol. Chem.* 275:16723-9) and tested by the same chemoinvasive assay. Expression of $Gb_3$ in OK cells significantly changed the cell phenotype. $Gb_3$-expressing OK cells formed filopodia on the leading edge of growing monolayers (FIG. 3G), similar to the phenotype seen in T-84, Caco-2 and HT-29 cells. Moreover, as shown by chemoinvasive assay FIG. 3H), the transfected OK cells penetrated through the filter. Importantly, only OK cells which expressed $Gb_3$ penetrated through the filter (FIG. 3H), while cells without $Gb_3$ from the same monolayer, and control cells transfected with empty plasmid did not migrate through the filter at all.

Example 5

$Gb_3$ Appears Earlier than $G_{M1}$ in Newly Developing Filopodia

Another way to test the significance of $Gb_3$ in development of cell invasive abilities is to treat them with agents that block glucosylceramide synthesis, such as threo-1-phenyl-2-palmitoylamino-3-morpholino-1-propanol (PMP) (Radin, N. S. (1999) *Biochem. Pharmacol.* 57:589-595). Therefore, the requirement for $Gb_3$ in the appearance of an invasive subpopulation in colon carcinoma monolayers was examined. Indeed, the presence of 10 μM PPMP in growth media completely eliminated the subpopulation of $Gb_3$ enriched cells with filopodia on the leading edge of sub-confluent Caco-2 and T-84 cells. This data indicates that $Gb_3$ and possibly other glucosylceramides are necessary for formation of Caco-2 invasive cells.

Figure 3:
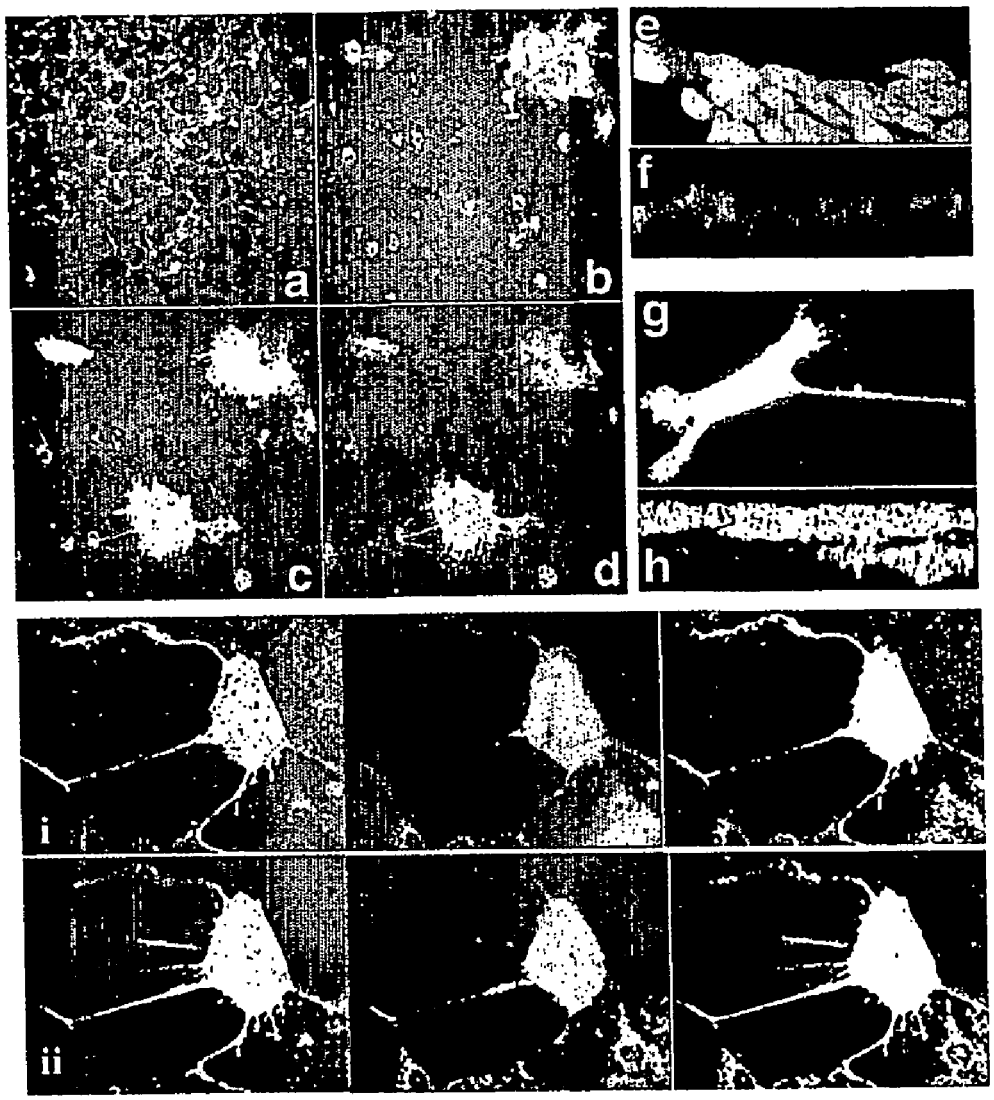
FIGS. 3A-3II depict a chemoinvasive assay. Confocal optical sections of Caco-2 and OK cells grown on Transwell filters from the top surface to bottom. Cells were stained with Stx1B-OrG to detect $Gb_3$ and CTB-TRITC (Cyto7) to detect $G_{M1}$.

To test whether $Gb_3$ plays a sufficient role in filopodia formation, or whether other GSLs are equally important, living Caco-2 cells were fluorescently labeled to visualize the distribution of $Gb_3$ and another abundant GSL, $G_{M1}$, and monitored over time to detect formation of new filopodia. As shown in FIG. 3I (left panel), $Gb_3$ is highly upregulated in cells with filopodia, compared to neighboring cells without filopodia. In contrast, the level of $G_{M1}$, expression (FIG. 3I, middle panel) is relatively equal in all monitored cells, and $G_{M1}$ does not colocalize with the $Gb_3$ pattern in the filopodia (FIG. 3I, right panel). In 75 minutes, new $Gb_3$-enriched filopodia appeared in monitored cell (FIG. 3II, left panel). The majority of these new filopodia do not yet contain any detectable amount of $G_{M1}$, (FIG. 3II, middle panel). These data indicate that $Gb_3$, but not $G_{M1}$, appears very early in formation of the Caco-2 invasive phenotype.

Example 6

Cytoskeletal Structure of Filopodia

Figure 4:
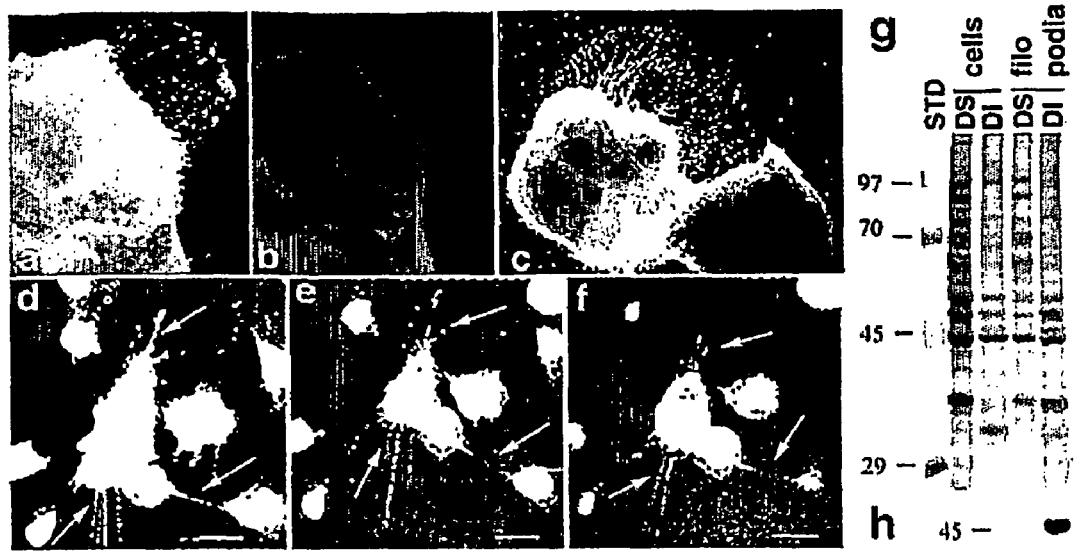
FIGS. 4A-4H depict the cytoskeletal elements of filopodia.

There are two different views of how cells spread and move (Mellman, I. (2000) *J. Cell Biol.* 149:529-530). One is based on directed actin polymerization that provides a physical force from within the cells that effectively pushes the cell forward (Vasioukhin, V. et al. (2000) *Cell* 100:209-219). The alternative pathway is based on microtubule assembly, as in the case of axonal growth (Baas, P. (1997) *Curr. Opinion Cell Biol.* 9:29-36). To test whether actin polymerization initiates Caco-2 filopodia formation, the distribution of $Gb_3$ and F-actin were visualized simultaneously. Surprisingly, filamentous actin was completely absent from many filopodia (FIGS. 4A and 4B). F-actin followed the $Gb_3$ pattern in some filopodia structures and co-localized with $Gb_3$, but never reached the tips of filopodia marked by $Gb_3$. Other evidence against F-actin involvement in filopodia formation is based on actin depolymerization. It has been shown that the specific inhibition of Rho kinase Y-27632 leads to dramatic reduction of F-actin with changes in epithelial cell geometry typical for perijunctional actin ring disruption (Kawada, N. et al. (1999) *Biochem. Bioph. Res. Com.* 266:296-300; Szaszi, K et al. (2000) *J. Biol. Chem.* 275:28599-606). Despite pronounced effects of 2 µg/ml Y-27632 on living Caco-2 cell morphology after 15-30 minuntes of treatment, the filopodia and filopodia-mediated cell-cell contacts did not change even after 60 minutes of exposure to the inhibitor FIGS. 4D-4F). Additionally, ezrin, which is involved in interaction of the actin cytoskeleton with plasma membrane to promote cell adhesion (Martin, M. et al. (1995) *J. Cell Biol.* 128:1081-1093), did not co-localize with $Gb_3$ in filopodia and in most cases did not follow the $Gb_3$ distribution pattern.

To test the alternate hypothesis that filopodia are microtubule-driven structures, sub-confluent Caco-2 cells were stained with antibody against α-tubulin. Immunofluorescence microscopy demonstrated the presence of α-tubulin in filopodia (FIG. 4C), which co-localized with the $Gb_3$ pattern over their entire length. In most eukaryotes, tubulin is subjected to several types of post-translational modification including palmitylation (Caron, J. M. (1997) *Mol. Biol. Cell* 8:612-636). Thus, in neuronal cells, tubulin is specifically linked to ganglioside $G_{M1}$, through its fatty-acid moiety (Palestini, P. et al. (2000) *J. Biol. Chem.* 275:9978-9985). Because microtubules and $Gb_3$ are co-localized in filopodia, it was possible that they form a protein-glycosphingolipid complex as occurs in neuronal cells. To test this possibility, filopodia were isolated from cell bodies by vibration, cell and filopodia proteins were divided into detergent soluble (DS) and insoluble (DIM) fractions, separated on SDS-AGE, and overlaid (FIG. 4G) with CD77 antibody against $Gb_3$. $Gb_3$-positive protein bands from the filopodia preparation, which appeared in the DIM fraction, were identified by MASS-spectroscopy (MS). Indeed, MS analysis identified one of these filopodia proteins as human β-tubulin II (FIG. 4H). These data demonstrate that tubulin polymerization, rather than F-actin, is responsible for the filopodia appearance in Caco-2 carcinoma cells, and that complex formation between β-tubulin and $Gb_3$ may play a crucial role in this process.

Example 7

Recombinant B-Subunit Alone Causes Apoptosis in Human Colon Cancer Cells

Figure 5:
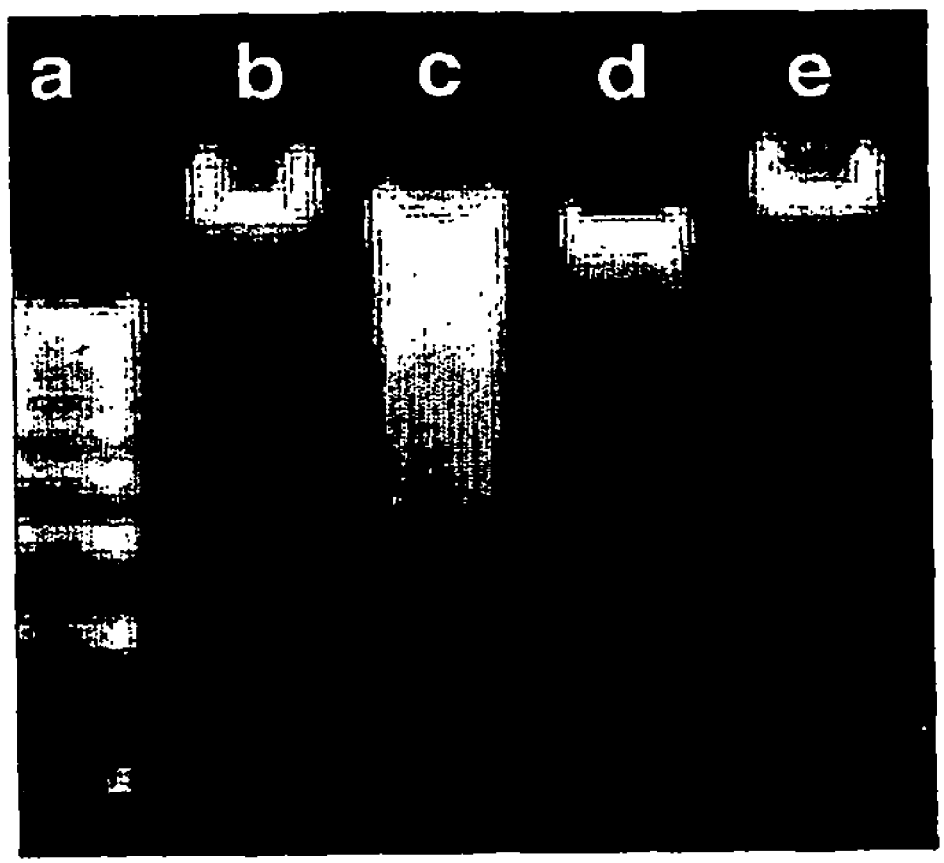
FIG. 5 depicts the apoptotic DNA fragmentation caused by Stx1B uptake in Caco-2 cells. Lane a: DNA-laddering markers. Lane b: Intact DNA from control (not Stx1B treated) cells. Lane c: DNA fragmentation from cells exposed to 0.5 μg/ml Stx1B for 48 hours. Lane d: Inhibition of apoptotic DNA fragmentation by 75 μM z-VAD fmk (a tripeptide inhibitor of a broad range of caspases) in cells exposed to 0.5 μg/ml Stx1B for 48 hours. Lane e: Intact DNA from cells incubated with 10 μg/ml B-subunit of Cholera toxin for 48 hours (negative control).

The ability of Stx1B alone to cause apoptosis in human colon cancer cells was measured by DNA fragmentation using the DNA-laddering assay. To test whether Stx1B caused DNA fragmentation, Caco-2 cells were incubated for 48 h with 0.5 µg/ml recombinant Stx1B. Same age cells from the same passage not exposed to Stx1B or exposed for 48 hours to 10 µg/ml Cholera Toxin B-subunit (CTB) were used as controls. As shown in FIG. 5, lane c, Stx1B internalization caused massive DNA fragmentation in Caco-2 cells, compared to intact non-fragmented DNA form cells not exposed to Stx1B (lane b) or incubated with CTB (lane e). To test whether Stx1B-triggered apoptosis is mediated through activation of caspases, Caco-2 cells were simultaneously exposed to both Stx1B for 72 hours and 75 µm z-VAD-fink, a tripeptide inhibitor of abroad range of caspases (Mancini, M. et al. (1998) *J. Cell Biol.* 140:1485-95). Inhibition of caspases decreased DNA fragmentation by Stx1B (lane d), indicating that caspases are involved in signal transduction in the Stx1B-triggered apoptotic response. This means that B-subunit can be involved in signal transduction, a new concept for AB toxins.

Example 8

Stx1B Selectively Kills $Gb_3$-Postive Cells only

To test whether Stx1B selectively causes apoptotic death in $Gb_3$-positive cells, T-84 cells, which have a heterogeneous cell population in terms of $Gb_3$ expression, were exposed to Stx1B for up to 168 hours. Mitochondria were used as a viability control. It is known that pro-apoptotic signal transduction and damage pathways converge on mitochondrial membranes to induce their permeabilization. Mitochondrial membrane permeabilization differentially affects the outer membrane, which becomes protein-permeable, and the inner membrane, which continues to retain matrix proteins yet dissipates the mitochondrial transmembrane potential (Finucane, D. M. et al. (1999) *Exp. Cell Res.* 251:166-174). It is known that tetramethylrodamine (TMRE), a cell-permeant cationic fluorescent dye, is accumulated by active mitochondria only due to the negative inner membrane potential, and does not accumulate in deenergized mitochondria, and is widely use to discriminate between apoptotic and non-apoptotic cells (Finucane, D. M. et al. (1999) *Exp. Cell Res.* 251:166-174).

Figure 6:
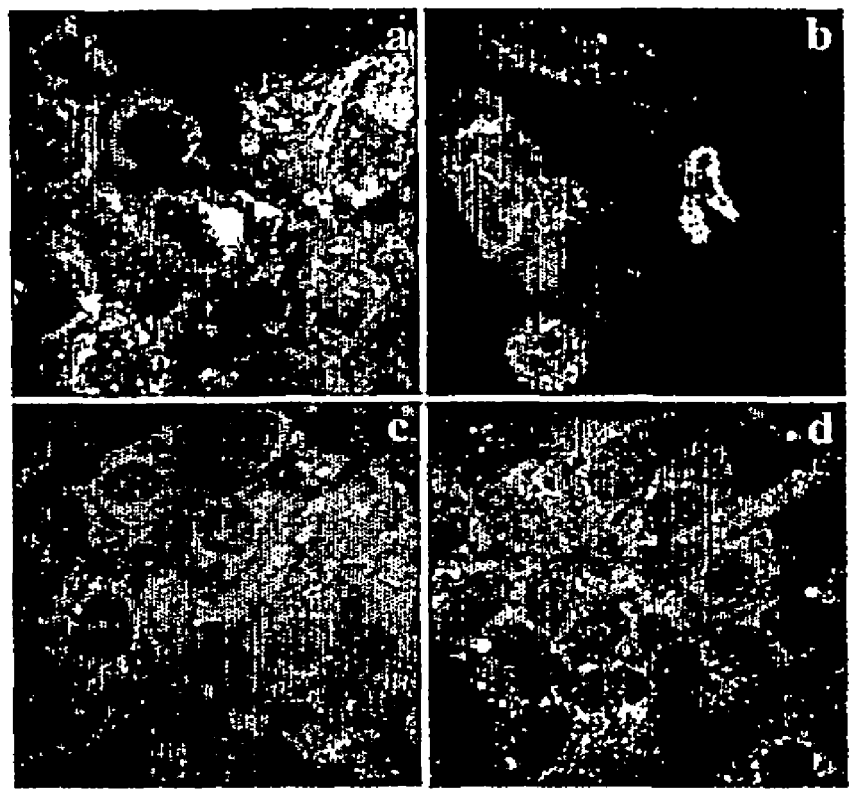
FIGS. 6A-6D depict the selective killing of $Gb_3$-positive cells after Stx1B uptake selectively. Confocal fluorescence images of T-84 and OK cells labeled with TMRE fluorescent dye to visualize mitochondria, Stx1B-OrG, and nuclear staining by Hoechst.

If Stx1B can selectively cause apoptosis in $Gb_3$-positive cells only, mitochondria in these cells would be depolarized in the cells shortly after Stx1B internalization and would not be detected by TMRE. The $Gb_3$-positive subpopulation of cells would then gradually disappear from T-84 monolayer. Moreover, T-84 cells, which lack $Gb_3$ would not be damaged by Stx1B and their mitochondria would remain active and could be visualized by TMRE. As shown in FIG. 6A, after 24 hours of exposure to Stx1B, virtually every cell that did not internalize Stx1B due to the absence of $Gb_3$ has active mitochondria. However, all cells that accumulated Stx1B already had inactive apoptotic mitochondria. Incubation of T-84 monolayers (FIG. 6B) with Stx1B for a longer amount of time (up to 168 hours) led to elimination of cells with internalized Stx1B. In contrast, in cells from the same monolayers that did not take up Stx1B due to the absence of $Gb_3$ receptors on the apical membrane, mitochondria remain active (FIG. 6B), which mean that they survived. Additionally, OK cells, which do not express $Gb_3$ and thus do not bind/internalize Stx1B, are resistant to Stx1B-mediated apoptosis and demonstrate active mitochondria in each cell even after 168 hours of exposure to Stx1KB (FIGS. 6C and 6D). This data demonstrates that Stx1B selectively causes apoptotic death in cells expressing glycosphingolipid $Gb_3$.

Example 9

Bcl-2 Protein is Downregulated Due to Stx1B-Caused Apoptosis

Figure 7:
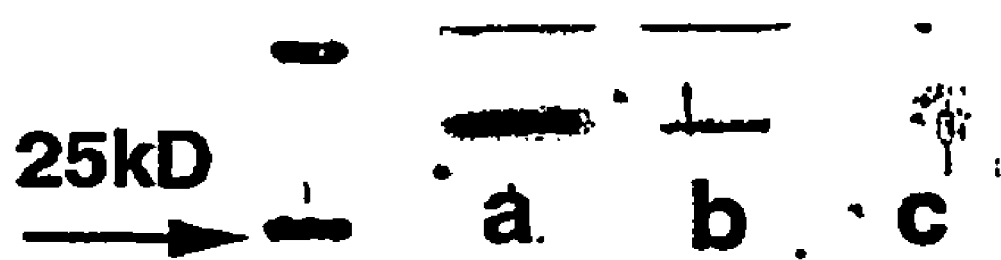
FIG. 7 depicts the downregulation of Bcl-2 caused by Stx1/Stx1B triggered apoptosis in Caco-2 cells. Lane a: The amount of Bcl-2 in control Caco-2 cells. Lane b: The amount of Bcl-2 in cells exposed to 0.5 μg/ml recombinant Stx1B for 48 hours. Lane c: The amount of Bcl-2 in cells exposed to 0.1 μg/ml Stx1 for 48 hours. Bcl-2 was detected in total cell lysate by Western blot using polyAb.

In classical mitochondria-dependent apoptosis, inner membrane depolarization is followed by complex signal transduction pathway, which causes changes in expression of pro- and antiapoptotic Bcl-family proteins (Adams, J. M. and Cory, S. (1998) Science 281:1322-1326). It has recently been shown that Stx1-mediated apoptosis in HEp-2 human laryngeal epithelial cells causes significant upregulation of proapoptotic Bax, while expression of another proapoptotic protein from this family Bak and antiapoptotic Blc-2 did not change from control (Krebs, J. F. (1999) J. Cell Biol. 144: 915-26). Human colon cancer cells were tested to determine whether they similarly respond to Stx1 or Stx1B. As shown on FIG. 7, both holotoxin and B-subunit decrease the amount of Bcl-2 protein in Caco-2 cells. This result confirms the involvement of mitochondrial Bcl proteins in the apoptotic cascade triggered by Stx1/Stx1B uptake and suggests significant differences in the apoptotic signal transduction pathway between intestinal Caco-2 and laryngeal epithelium.

Example 10

Stx1B Treatment Significantly Inhibits Tumor Growth in a Nude Mouse Model

Figure 8:
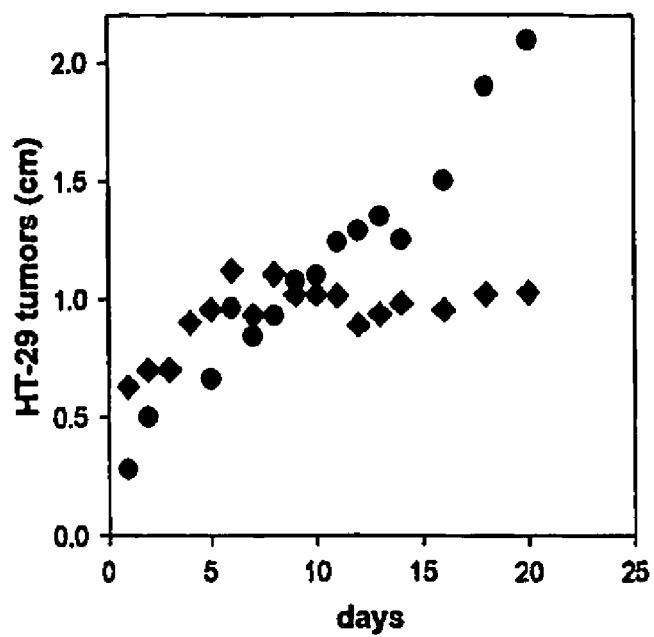
FIG. 8 depicts an example of a typical inhibition of HT-29 colon cancer cell tumor growth by Stx1B in live mice. Tumor was produced in both flanks of mice. Tumor in one flank was injected with Stx1B, the other flank was not treated. Nontreated tumor (circles) substantially overgrow Stx1B-treated tumor (diamonds). In fact, injected toxin stopped tumor enlagement.

To test whether Stx1B has the apoptotic effects described above on growing colonic tumors, a nude mouse xenograph model was used. Briefly, nude mice (n=11 animals) were injected subcutaneously into flanks with $10^7$ HT-29 human colon cancer cells. When tumors reached 0.3 cm in size, the mice were divided into three groups: two control groups, in which tumors were not treated at all or were injected with phosphate buffered saline (PBS) only, and a third group, in which tumors were injected with a non-toxic dose of Stx1B (n=8 flanks). Animals were monitored over seven weeks until control tumors reached ~1 cm in size, when animals have to be euthanized. As shown in FIG. 8, Stx1B injections significantly inhibited tumor growth in nude mice.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method of reducing, or inhibiting invasiveness and metastasis of tumor cells in a subject, wherein the tumor cells produce $Gb_3$, comprising administering to the subject a therapeutically effective amount of a Stx1B-subunit of Shiga toxin.

2. The method of claim 1, wherein the tumor cells are colon tumor cells.

3. The method of claim 1, wherein the tumor cells are from a tissue selected from the group consisting of: colon, lung, brain, skin, ovary, pancreas, liver, stomach, bladder, bone, testicle, uterus, adipose tissue, throat, kidney, tongue, pituitary gland, thyroid, lymphoid tissue, eye, and cervix.

4. The method of claim 1, wherein the therapeutically effective amount of the Stx1B-subunit of Shiga toxin is administered prior to the onset of metastasis by the tumor cells.

5. The method of claim 1, wherein the therapeutically effective amount of the B-subunit of Shiga toxin is administered subsequent to the onset of metastasis by the tumor cells.

6. The method of claim 1, further comprising administering to the subject a therapeutically effective amount of radiation.

7. The method of claim 1, further comprising administering to the subject a therapeutically effective amount of at least one chemotherapeutic agent.

8. The method of claim 1, wherein the subject is a human.

9. The method of claim 1, wherein the Stx1B-subunit of Shiga toxin is conjugated to a therapeutic moiety.

10. A method of reducing, or inhibiting invasiveness and metastasis of colon tumor cells in a subject, wherein the tumor cells produce $Gb_3$, comprising administering to the subject a therapeutically effective amount of a Stx1B-subunit of Shiga toxin.

* * * * *